(12) United States Patent
Besemer et al.

(10) Patent No.: US 6,391,623 B1
(45) Date of Patent: *May 21, 2002

(54) FLUIDICS STATION INJECTION NEEDLES WITH DISTAL END AND SIDE PORTS AND METHOD OF USING

(75) Inventors: Donald Besemer, Los Altos Hills; Peter E. Lobban, Mountain View; Michael C. Norris, Santa Clara; Steven V. Muller, Mountain View, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/501,095

(22) Filed: Feb. 9, 2000

Related U.S. Application Data

(63) Continuation of application No. 09/070,689, filed on Apr. 30, 1998, now Pat. No. 6,114,122, which is a continuation-in-part of application No. 08/624,312, filed on Mar. 26, 1996, now abandoned.

(51) Int. Cl.[7] .......................... C12M 1/34; C12Q 1/68; C12P 19/34; C07H 21/04; G01N 33/566
(52) U.S. Cl. ........................ 435/287.2; 435/6; 435/7.1; 435/91.1; 435/91.2; 435/283.1; 435/285.1; 536/23.1; 536/24.3; 536/24.31; 536/24.32; 536/24.33; 422/100; 436/501
(58) Field of Search ................ 435/6, 7.1, 91.1, 435/91.2, 283.1, 285.1, 285.2, 286.2, 286.6, 286.7, 287.2, 287.3; 536/23.1, 24.3, 24.31, 24.32, 24.33; 422/100; 604/170.01, 171, 158; 222/81; 436/501

(56) References Cited

U.S. PATENT DOCUMENTS

| | | | |
|---|---|---|---|
| 4,665,034 A | 5/1987 | Chandler | 435/287 |
| 4,764,671 A | 8/1988 | Park | 250/227 |
| 4,829,010 A | 5/1989 | Chang | 422/58 |
| 4,859,419 A | 8/1989 | Marks et al. | 422/56 |
| 4,889,611 A | 12/1989 | Blough | 204/409 |
| 5,098,389 A | * 3/1992 | Cappucci | 604/158 |
| 5,104,808 A | 4/1992 | Laska et al. | 436/48 |
| 5,143,854 A | 9/1992 | Pirrung et al. | 436/518 |
| 5,154,888 A | 10/1992 | Zander et al. | 422/58 |

(List continued on next page.)

FOREIGN PATENT DOCUMENTS

| | | |
|---|---|---|
| WO | WO 89/10977 | 11/1989 |
| WO | WO 89/11548 | 11/1989 |
| WO | WO 90/15070 | 12/1989 |
| WO | WO 93/09668 | 5/1992 |
| WO | WO 92/10092 | 6/1992 |
| WO | WO 95/33846 | 12/1995 |

OTHER PUBLICATIONS

Fodor et al., "Light–Directed, Spatially Addressable Parallel Chemical Synthesis", *Science*, 251:767–777 (1991).

*Physical Acoustics, Principles and Methods.* vol. 2, Part B, Mason, ed., Academic Press, (1965).

*Piezoelectric Technology, Data for Engineers*, Clevite Corp.

Sjolander et al. Anal Chem. vol. 63 pp. 2338–2345, 1991.

*Primary Examiner*—Jeffrey Siew
(74) *Attorney, Agent, or Firm*—Townsend and Townsend and Crew LLP

(57) ABSTRACT

The present invention generally provides novel apparatuses for rapidly and efficiently carrying out repeated hybridizations of a target nucleic acid to an array of nucleic acid probes. The apparatus generally includes a fluid delivery system, a fluid mixing system, a temperature control system and a process control system integrated into a single device.

34 Claims, 11 Drawing Sheets

Microfiche Appendix Included
(3 Microfiche, 210 Pages)

U.S. PATENT DOCUMENTS

| | | | |
|---|---|---|---|
| 5,170,659 A | 12/1992 | Kemp | 73/46 |
| 5,229,297 A | 7/1993 | Schniplesky et al. | 436/94 |
| 5,230,866 A | 7/1993 | Shartle et al. | 422/103 |
| 5,258,781 A | 11/1993 | John | 346/140 |
| 5,279,721 A | 1/1994 | Schmid | 204/182.8 |
| 5,288,463 A | 2/1994 | Chemelli | 422/58 |
| 5,296,195 A | 3/1994 | Pang et al. | 422/82.05 |
| 5,352,609 A | 10/1994 | Bouqet et al. | 435/270 |
| 5,384,261 A | 1/1995 | Winkler et al. | 436/518 |
| 5,395,587 A | 3/1995 | Brigham-Burke et al. | 422/68.1 |
| 5,422,271 A | 6/1995 | Chen et al. | 435/287 |
| 5,424,186 A | 6/1995 | Fodor et al. | 536/22.1 |
| 5,486,335 A | 1/1996 | Wilding et al. | 422/55 |
| 5,489,678 A | 2/1996 | Fodor et al. | 536/22.1 |
| 5,500,187 A | 3/1996 | Deoms et al. | 422/58 |
| 5,543,329 A | 8/1996 | Bedell | 435/7.32 |
| 5,543,884 A * | 8/1996 | Earle et al. | 354/324 |
| 5,578,832 A | 11/1996 | Trulson et al. | 250/458.1 |
| 5,587,128 A | 12/1996 | Wilding et al. | 422/250 |
| 5,593,838 A | 1/1997 | Zanzucchi et al. | 435/6 |
| 5,593,839 A | 1/1997 | Hubbell et al. | 435/6 |
| 5,595,908 A | 1/1997 | Fawcett et al. | 435/287.2 |
| 5,599,504 A | 2/1997 | Hosoi et al. | 422/82.08 |
| 5,627,027 A * | 5/1997 | Waggoner et al. | 435/6 |
| 5,627,041 A | 5/1997 | Shartle | 435/7.24 |
| 5,635,358 A | 6/1997 | Wilding et al. | 435/7.2 |
| 5,637,469 A | 6/1997 | Wilding et al. | 435/7.2 |
| 5,652,149 A | 7/1997 | Mileaf et al. | 435/518 |
| 5,658,802 A | 8/1997 | Hayes et al. | 436/518 |
| 5,674,743 A | 10/1997 | Ulmer | 435/287.2 |
| 5,675,700 A | 10/1997 | Atwood et al. | 392/382 |
| 5,683,916 A | 11/1997 | Goffe et al. | 436/535 |
| 5,698,450 A | 12/1997 | Ringrose et al. | 436/525 |
| 5,716,825 A | 2/1998 | Hancock et al. | 435/286.5 |
| 5,726,010 A | 3/1998 | Clark | 435/5 |
| 5,726,013 A | 3/1998 | Clark | 435/5 |
| 5,812,511 A | 9/1998 | Kawamura et al. | 369/77.2 |
| 5,869,004 A | 2/1999 | Parce et al. | 422/100 |
| 6,114,122 A * | 9/2000 | Besemer et al. | 435/6 |

* cited by examiner

FLUIDICS STATION INJECTION NEEDLES WITH DISTAL END AND SIDE PORTS AND METHOD OF USING

CROSS REFERENCE TO RELATED APPLICATIONS

The present application is a continuation of Ser. No. 09/070,689, filed Apr. 30, 1998, now U.S. Pat. No. 6,114,122, issued Sep. 5, 2000, which is a continuation-in-part of Ser. No. 08/624,312, filed Mar. 26, 1996, now abandoned, the complete disclosures of which are incorporated herein for all purposes. The present invention generally provides novel apparatuses for rapidly and efficiently carrying out repeated hybridizations of a target nucleic acid to an array of nucleic acid probes. The apparatus generally includes a fluid delivery system, a fluid mixing system, a temperature control system and a process control system integrated into single device.

MICROFICHE APPENDIX

A microfiche appendix including 3 sheets with 210 frames is included herewith. The microfiche appendix was also included with co-pending Application Ser. No. 08/624,312, previously incorporated by reference.

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyrights whatsoever.

BACKGROUND OF THE INVENTION

Oligonucleotide probes have long been used to detect complementary nucleic acid sequences in a nucleic acid of interest (the "target" nucleic acid). In some assay formats, the oligonucleotide probe is tethered, i.e., by covalent attachment to a solid support, and arrays of oligonucleotide probes immobilized on solid supports have been used to detect specific nucleic acid sequences in a target nucleic acid. See, e.g., published PCT Application Nos. WO 89/10977 and 89/11548.

The development of VLSIPS™ technology has provided methods for making very large arrays of polymer sequences, including polypeptides and polynucleotides, on very small substrates. See U.S. Pat. No. 5,143,854 and published PCT Application Nos. WO 90/15070 and 92/10092, each of which is incorporated herein by reference in its entirety for all purposes. U.S. patent application Ser. No. 08/082,937, filed Jun. 25, 1993, now abandoned, describes methods for making arrays of oligonucleotide probes that can be used to provide the complete sequence of a target nucleic acid and to detect the presence of a nucleic acid containing a specific nucleotide sequence. Microfabricated arrays of large numbers of oligonucleotide probes, called GeneChips® microfabricated arrays, offer great promise for a wide variety of applications, e.g., sequencing-by-hybridization techniques (SBH) and diagnostic methods for detecting genetic and other disorders.

A major consideration in nucleic acid hybridization analyses using these arrays, as well as with other methods, is the rate at which that hybridization occurs. This hybridization rate can be affected by a variety of conditions, including the concentration of the target nucleic acid in the sample, the temperature of the hybridization reaction, the composition of the hybridization solution and others. In addition, hybridization reactions in oligonucleotide array formats are also affected by the level of mixing of the target nucleic acid during the hybridization. Such mixing typically results in the presentation of a maximal amount of target nucleic acid to the probes on the surface of the array.

Given the increased efficiency of VLSIPS™ based hybridization analyses, it is desirable to provide integrated devices which are capable of optimizing a number of the specific conditions of these hybridization reactions. In particular, it would be desirable to provide a hybridization apparatus which is capable of delivering a sample to an array, mixing the sample during hybridization, maintaining the sample at an optimal temperature for hybridization, and removing the sample from the chamber following the hybridization. The present invention meets these and other needs.

SUMMARY OF THE INVENTION

The present invention generally provides novel apparatuses for rapidly and efficiently carrying out repeated hybridizations of a target nucleic acid to an array of nucleic acid probes. The apparatuses of the invention typically include a fluid delivery system for delivering and injecting selected fluids into an array cartridge or package which includes a hybridization chamber having a polymer array incorporated therein. Also included in some embodiments of the apparatuses of the invention is a mounting system for holding the hybridization chamber within the array cartridge in fluid communication with the fluid delivery system. The apparatuses also include a fluid mixing system for mixing the fluids within the hybridization chamber, a temperature control system for monitoring and controlling the temperature of the fluids within the hybridization chamber, and a process control system for monitoring and selectively controlling the fluid delivery system, the fluid mixing system and the temperature control system.

DETAILED DESCRIPTION OF THE INVENTION

I. Introduction

Figure 1:
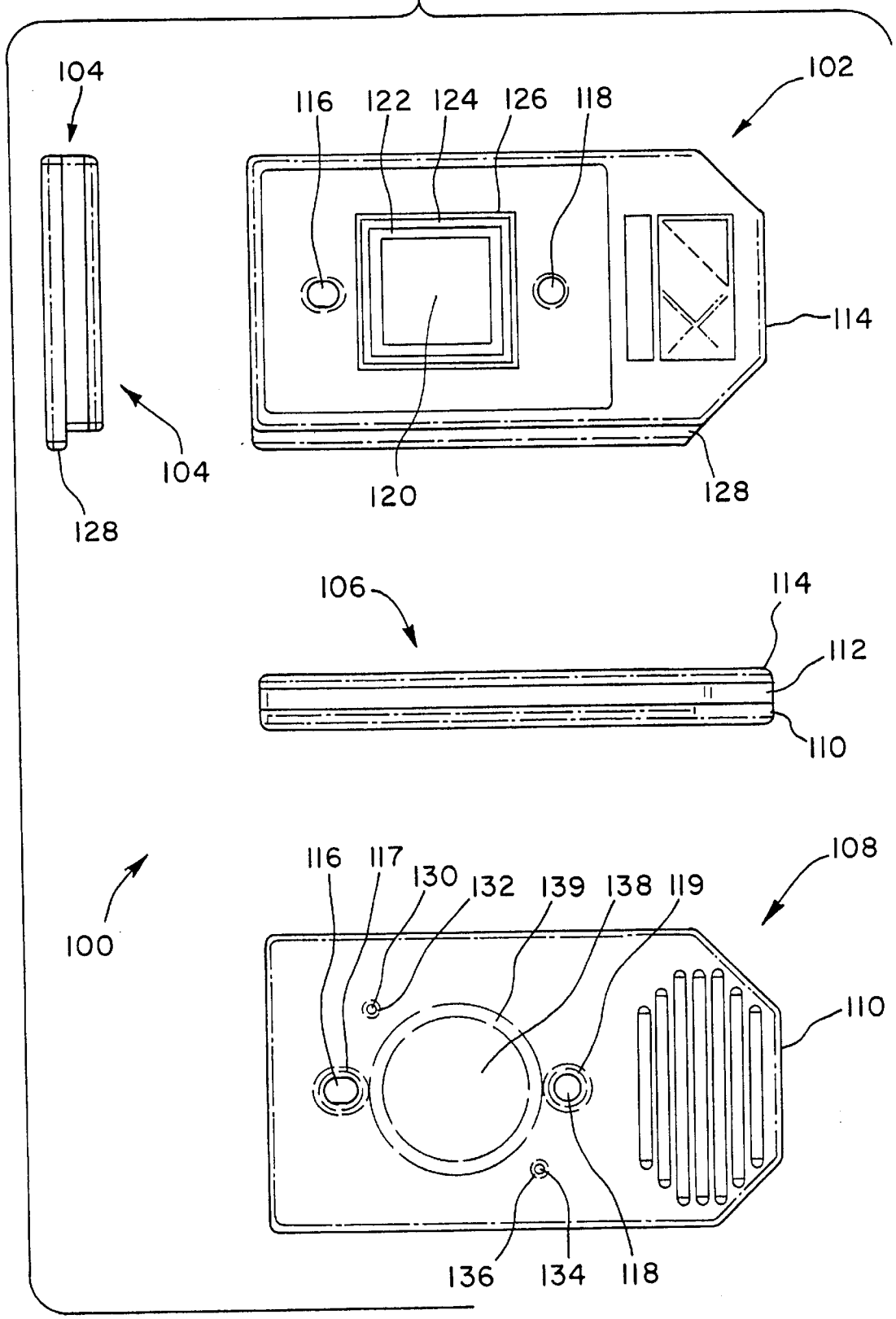
FIG. 1 shows an illustration of a polymer array cartridge device from a top view, end view, side view and bottom view.

It is a general object of the present invention to provide an apparatus for rapidly and efficiently carrying out repeated, controlled hybridization reactions with polymer arrays. Generally, the apparatuses described herein are termed "fluidics stations." However, the terms "hybridization stations" or "hyb stations" are also used as these devices are often used in conducting hybridization reactions. To accomplish the above, the fluidics stations described herein generally include a fluid delivery system for delivering a sample or wash solution to a hybridization reaction chamber, a fluid mixing system for mixing the sample within the hybridization chamber and/or rinsing the chamber, a temperature control system for monitoring and controlling the temperature of the hybridization reaction chamber and a process control system for operating each of these individual systems according to a preprogrammed operating profile.

The fluidics stations described herein are generally useful for performing hybridization reactions with polymer arrays. However, the fluidics stations may also find use in areas such as staining a hybridization array, washing a hybridization array or a stained array, recovering sample from a hybridization array, recovering stain from a stained array, and the like. In preferred aspects, the polymer arrays are oligonucleotide arrays which include a plurality of different oligonucleotides coupled to a solid substrate in different known locations. Such polymer arrays have been previously described in, e.g., U.S. Pat. No. 5,143,854, Published PCT Application Nos. WO 90/15070 and 92/10092. These pioneering arrays may be produced using mechanical or light directed synthesis methods which incorporate a combination of photolithographic methods and solid phase oligonucleotide synthesis methods. See Fodor et al., Science, 251:767–777 (1991), Pirrung et al., U.S. Pat. No. 5,143,854 (see also PCT Application No. WO 90/15070) and Fodor et al., PCT Publication No. WO 92/10092, all incorporated herein by reference. These references disclose methods of forming vast arrays of peptides, oligonucleotides and other polymer sequences using, for example, light-directed synthesis techniques. Techniques for the synthesis of these arrays using mechanical synthesis strategies are described in, e.g., PCT Publication No. 93/09668 and U.S. Pat. No. 5,384,261, each of which is incorporated herein by reference in its entirety for all purposes.

Although generally described in terms of hybridization reactions and more specifically, nucleic acid hybridizations, it should be appreciated that a variety of reactions may be performed using the fluidics stations of the present invention, including, e.g., extension or amplification reactions using tethered probes as template or primer sequences, screening of receptors against arrays of small molecules, peptides or peptidomimetics, polymerase chain reactions (PCR) with primer and template in solution, and the like.

II. Fluidics Station

A. Array Cartridge

As described above, the fluidics stations described herein are typically intended for use with polymer arrays. In particularly preferred aspects, the fluidics stations are used in conjunction with arrays that are packaged within a housing, like those described in, e.g., Published PCT Application No. WO 95/33846, which is incorporated herein by reference in its entirety for all purposes. In brief, the housing typically includes a body having a reaction cavity disposed therein. The array or substrate is mounted over the cavity on the body such that the front side of the array substrate, i.e., the side upon which the array has been synthesized, is in fluid communication with the cavity. The bottom of the cavity may optionally include a light absorptive material, such as a glass filter or carbon dye, to prevent impinging light from being scattered or reflected during imaging by detection systems. This feature improves the signal-to-noise ratio of such systems by significantly reducing the potential imaging of undesired reflected light.

The cartridge also typically includes fluid inlets and fluid outlets for flowing fluids into and through the cavity. A septum, plug, or other seal may be employed across the inlets and/or outlets to seal the fluids in the cavity. The cartridge also typically includes alignment structures, e.g., alignment pins, bores, and/or an asymmetrical shape to ensure correct insertion and/or alignment of the cartridge in the assembly devices, fluidics stations, and reader devices.

An illustration of one embodiment of the array cartridge 100 is shown in FIG. 1. FIG. 1 shows a top view 102, end view 104, side view 106 and bottom view 108 of the array cartridge 100. The body of the array cartridge may generally be fabricated from one or more parts or casings 110–114 that are made using a number of manufacturing techniques. In preferred aspects, the cartridge is fabricated from two or more injection molded plastic parts. Injection molding enables the parts to be formed inexpensively. Also, assembling the cartridge from two or more parts simplifies the construction of various features, such as the internal channels for introducing fluids into the cavity. As a result, the cartridges may be manufactured at a relatively low cost.

The top and bottom views of the cartridge optionally include alignment structures, such as alignment holes 116 and 118. As shown, these alignment holes are disposed through the body of the cartridge, however, those of ordinary skill will appreciate that other alignment structures, e.g., alignment pins, etc., would be equally useful. As shown in the bottom view 108, alignment holes 116 and 118 also include an annular beveled region to assist in insertion of complementary alignment pins on the fluidics station. In a preferable embodiment, alignment occurs by inserting injection needles into the septa of the inlet and outlet ports without the use of holes 116 and 118, as described hereinafter.

Referring to the top view 102 of the cartridge 100, cavity 120 includes a flat bottom peripheral portion 122, a beveled portion 124 extending from the flat bottom peripheral portion, and a flat upper portion 126 surrounding the beveled portion. The array includes an outer periphery which rests against the flat bottom peripheral portion 122. The beveled portion aligns the chip onto the flat bottom peripheral portion 122. As shown, the bottom casing 110 extends outside the middle and top casings, 112 and 114, respectively, to provide a non flush edge 128. The alignment structures 116 and 118, as well as the non flush edge 128, ensure proper orientation of the cartridge in the fluidics station, as well as other devices used in producing and reading polymer arrays. Surrounding mounting structures 116 and 118 are annular recesses 117 and 119, respectively which aid in guiding the cartridge onto complementary mounting structures on the various devices employed in the manufacture and use of the cartridges.

As shown in the bottom view 108, the cartridge includes inlet and outlet ports 130 and 134, which include a beveled annular region 132 and 136 surrounding these ports, respectively, to assist with fluid flow therethrough. Typically, the inlet and outlet ports will include septa disposed across the ports (not shown). Bottom casing 110 also includes a cavity 138, located adjacent the array, which cavity may be adapted for receiving a temperature monitoring and/or controlling device. As shown the cavity 138 has an annular recessed region 139 surrounding it, to ensure that the temperature controller may be inserted with maximum ease.

The cavity 120 is preferably located at a center of the bottom casing, but may also be at other locations. The cavity may be round, square, rectangular, or any other shape, and may have any orientation. The cavity is preferably smaller than the surface area of the array chip to be placed thereon, and has a volume sufficient to perform hybridization and the like. In one embodiment, the cavity includes dimensions such as a length of about 0.6 inch, a width of about 0.6 inch and a depth of about 0.07 inch.

In a preferred embodiment, the top casing with selected cavity dimensions may be removed from the middle and bottom casings, and replaced with another top casing having different cavity dimensions. This allows for the attachment of an array chip. having a different size or shape by changing the top casing, thereby providing ease in using different chip sizes, shapes, and the like. Of course, the size, shape, and orientation of the cavity will often depend upon the particular application.

The array substrate segment may be attached to the body of the cartridge using a variety of methods. In preferred aspects, the array is attached using an adhesive. Preferred adhesives are resistant to degradation under conditions to which the cartridge will be subjected. In particularly preferred aspects, an ultraviolet cured adhesive attaches the array to the cartridge. Devices and methods for attaching the array are described in, e.g., Published PCT Application No. WO 95/33846.

A variety of modifications can be incorporated in the packaging methods and devices that are generally described herein, and these are generally outlined in greater detail in Published PCT Application No. WO 95/33846, previously incorporated by reference.

B. Fluid Delivery System

As described above, the fluidics station of the present invention typically includes a fluid delivery system for delivering a sample-containing fluid, a wash fluid, a buffer, or the like, to a hybridization chamber which contains a polymer array. The fluid delivery system generally includes a pump for moving the fluid, a valve assembly and manifold or tubing for selectively directing one or more different fluids to the array, and an injection system for introducing the fluid into the hybridization chamber.

Figure 2:
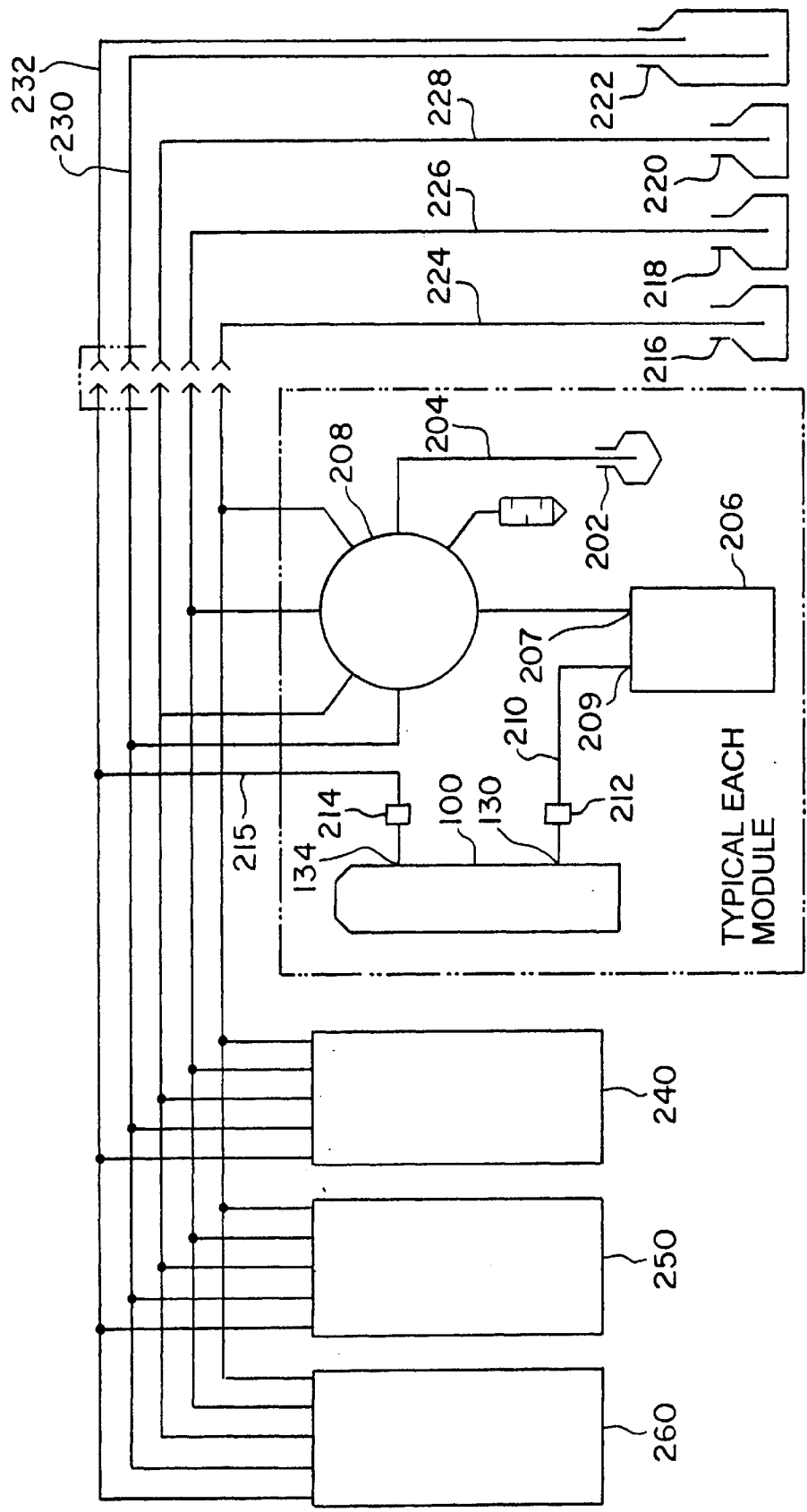
FIG. 2 shows a schematic illustration of one embodiment of a fluid delivery system incorporated into a hybridization fluidics station of the present invention.

A schematic illustration of one embodiment of a fluid delivery system which can be incorporated into the fluidics station of the present invention is shown in FIG. 2. In particular, the illustrated fluid delivery system includes a pump 206 for transporting fluids through the system. Generally, a number of different pump types may be used to deliver fluids to the hybridization chamber. For example, peristaltic pumps may be readily and inexpensively obtained from commercial sources and used in the delivery system. Positive displacement pumps, e.g., syringe pumps, may also be incorporated into the fluid delivery system. In alternative embodiments, gas-pressure fluid delivery systems may be incorporated to move fluids through the system. Preferably, the present invention employs a peristaltic pump 206 as shown in more detail in FIG. 3A.

As shown in FIG. 2, the fluid delivery system includes a pump 206 which is fluidly connected via a first port 207 to valve assembly 208, which is in turn, fluidly connected to a plurality of reagent vessels 202, 216–220, via tubes 204 and 224–228, respectively. A second port 209 of pump 206 is fluidly connected to a first inlet/outlet port 130 on the hybridization chamber or array cartridge 100, via fluid passage 210 which may optionally include a fluid sensor 212. Because the array cartridge is inserted into the fluidics station, this fluid connection is typically made through an injection needle present at the terminus of the inlet tube 210. Upon mounting the cartridge on the fluidics station, the injection needle is inserted into a fluid inlet/outlet port 130 on the cartridge. The second inlet/outlet port 134 of the hybridization chamber is fluidly connected to a waste vessel 222 via outlet tube 215 and waste line 232. Again, the fluid connection is typically made via a needle at the terminus of the outlet tube 215, which needle is inserted into the outlet port of the cartridge when the cartridge is mounted on the fluidics station. Outlet tube 215 may also incorporate a fluid sensor 214, as well.

Typically, pump 206 having a first port 207 and a second port 209, is fluidly connected to a number of reagent vessels 202 and 216–220 through a valve assembly 208 which allows for selected fluid connection with an individual selected reagent vessel. For example, when a sample is to be injected into the hybridization chamber/array cartridge 100, the valve assembly 208 is opened to provide a fluid connection between pump 206 and sample vessel 202, via sample tube 204. For other operations, e.g., washing or pre-scanning operations, the valve may be opened to selectively provide a fluid connection to one of the remaining reagent vessels 216–220, or to a waste vessel 222. Generally, multiport distribution valves are preferred for use as the valve assembly, however, multiple independent valves combined with a manifold system can also be employed.

Outlet 209 of pump 206 is fluidly connected to the first inlet/outlet port 130 of the hybridization chamber 100 via tube 210. As described above, inlet and outlet tubes 210 and 215, respectively, typically include injection needles at their termini for insertion into the inlet and outlet ports of the array cartridge which includes the hybridization chamber. These needles may be inserted into the inlet and outlet ports when the array cartridge is mounted upon the fluidics station, or alternatively, the needles may include a retraction mechanism which allows mounting of the array on the fluidics station without the needles being inserted into the inlet/outlet ports. The needles may then be inserted into the ports by operation of the retraction mechanism which extends the needles into the ports. A variety of mechanisms may be used for the retraction mechanism including a lever and cam assembly, whereby when the lever is operated, the cam displaces a frame upon which the needles are mounted in the direction of the ports. In alternative aspects, pressure seals may be employed which provide a sealed fluid connection between the inlet and outlet ports on the cartridge and their respective tubes, when the cartridge is mounted on the fluidics station.

To ensure proper filling of the hybridization chamber, the fluid delivery system may include sensors which indicate when the hybridization chamber has been completely filled with the selected fluid. As shown, sensors 212 and 214 are incorporated into the fluid delivery tube 210 and fluid outlet tube 215, respectively. A variety of sensor types may be used to detect the presence of the delivered fluid, such as conductivity sensors, optical sensors, thermal sensors and the like. In particularly preferred aspects, conductivity sensors are used. In brief, the sensors detect a change in the conductivity of the medium between two contact points in the sensor. As sample and wash solutions typically incorporate an elevated level of buffers and salts, their presence can be indicated by an increase in conductivity. In operation, pump 106 continues to fill the hybridization chamber 100 with a selected fluid until a change in conductivity is detected at sensor 214, indicating that the hybridization chamber is filled, at which time the pump is turned off.

In alternate aspects, the pump may simply be operated for sufficient time to deliver an appropriate volume of fluid to the hybridization chamber to ensure proper filling. This may typically be used in those embodiments that incorporate, e.g., positive displacement pumps or other easily calibrated pumping devices.

In delivering other fluids to the reaction chamber, e.g., wash solutions, scanning buffers, water, etc., the valve assembly 208 is configured to fluidly connect the pump 206 with a selected reagent vessel 216, 218, or 220. These solutions may then be delivered to the hybridization chamber for preselected time periods, or until the sensor indicates that a sufficient amount of fluid has been delivered, e.g., by sensing when a change in the conductivity or an optical characteristic of the solution flowing from the hybridization chamber has occurred.

Typically, the fluid delivery system will include a waste vessel 222. Fluids flowing out of the array cartridge via outlet tube 215 flow through waste tube 232 and into waste vessel 222. Additionally, waste tube 230 will typically be coupled to valve assembly 208. This can allow the fluid delivery system to be rinsed between operations while by-passing and avoiding contamination of the array cartridge where, for example, a positive displacement pump is used.

The fluid delivery system may also include a bypass for flowing fluid through the entire system when no cartridge is placed in the device. Typically, the bypass will include a fluid passage contained within the mounting door of the device, described in greater detail below, which passage is adapted to connect fluidically with the inlet/outlet tubes of the fluid delivery system and provide a fluid connection between the two tubes in the absence of a cartridge in the device.

C. Mixing System

Hybridization reactions in oligonucleotide array formats can generally be affected by the level of mixing of the target ligand, e.g., nucleic acid, during the hybridization. Such mixing typically results in the presentation of a maximal amount of target ligand to the polymer probes on the surface of the array. Accordingly, in addition to the fluid delivery system described above, the fluidics station also typically includes a system for mixing fluids that are introduced into the array cartridge. A variety of techniques may generally be employed for mixing a sample once it is introduced into an array cartridge.

In a first embodiment, the contents of the hybridization chamber are mixed by agitation. Generally, this involves moving the array cartridge with sufficient force and/or velocity to achieve appropriate mixing. Typically, a bubble will be introduced with the fluid sample to aid in the movement of the fluid during agitation. In general, rotation of the cartridge, or lateral shaking of a flat-lying array cartridge are sufficient for adequate mixing. Despite the apparent simplicity of the use of agitation, many difficulties arise in producing a functional device incorporating such agitation. For example, fluid connections generally must be provided from a flexible material, allowing movement of the array without translation of that motion to elements external to the array. In addition, temperature monitoring and control elements generally must be connected via similarly flexible connections.

In an alternate embodiment, fluid mixing within the hybridization chamber may be supplied using ultrasonic techniques that are generally known in the art. In particular, an ultrasonic element may be placed in contact with an external surface of the hybridization chamber such that an ultrasonic signal may be transmitted into the chamber, thereby providing convection of the fluid within the chamber. Examples of such ultrasonic elements include PZT elements made from a ceramic containing lead, zirconium and titanium. See, e.g., *Physical Acoustics, Principles and Methods*, Vol. I, (Mason ed., Academic Press, 1965), and Piezoelectric Technology, Data for Engineers, available from Clevite Corp.

Ultrasonic mixing generally requires near complete contact between the PZT element and the external surface of the hybridization chamber. As such, the PZT element will typically have a fluid layer disposed between the element and the external surface of the hybridization chamber or cartridge, e.g., water. The fluid layer may be deposited directly on the external surface of the cartridge, or may be incorporated within a membrane, e.g., a latex balloon, having one surface in contact with the external surface of the hybridization chamber and another surface in contact with the PZT element. An appropriately programmed computer may be used to control the application of a voltage to the PZT element, via a function generator and RF amplifier.

In alternative aspects, mixing of fluid within the hybridization chamber may be accomplished by bubbling gas through the hybridization chamber. Typically, this involves the flowing of an inert gas stream through the inlet port and out through the outlet port of the hybridization chamber. Preferred gases will not have any effect on hybridization rates or intensities, and include, e.g., argon, nitrogen and the like.

In particularly preferred embodiments, mixing of fluids within the hybridization chamber is supplied using a "drain and fill" method. Such methods typically involve alternately reversing the direction of the system's pump to drain and then fill the hybridization chamber. This is repeated as desired to achieve optimal hybridization of the target ligand to the polymer array. Reversal or stopping of the pump is generally triggered by the fluid sensors within the inlet and outlet tubes. For example, referring to FIG. 2, the hybridization chamber 100 is filled until fluid is detected at fluid sensor 214, indicating that the chamber is filled. At preselected intervals, the pump is then reversed, drawing the fluid from the chamber through the inlet/outlet port 130. When the fluid is drawn past fluid sensor 212, the sensor detects the lack of fluid at the sensor and triggers reversal of the pump, which then refills the chamber. This is repeated according to a preset time schedule and profile.

Alternatively, the fluid may be pumped through chamber 100 in an open loop. With such a configuration, the pump is actuated for a time sufficient to pass the required volume of fluid through chamber 100. Such an alternative is particularly useful when using de-ionized water.

D. Temperature Control System

The fluidics stations of the present invention also generally incorporate temperature monitoring and control systems for optimization of hybridization conditions. Typically, the temperature control system operates to maintain the temperature within the hybridization chamber at optimized levels, according to a preselected temperature profile. Temperature control may be carried out by a variety of means. For example, miniature temperature controllers and temperature sensors may be incorporated directly into the hybridization chamber within the array cartridge. Alternatively, the entire array cartridge may be placed in an environment that reflects the desired temperature, e.g., a temperature controlled compartment or water bath.

In preferred aspects, temperature monitoring and control is carried out by placement of a temperature control block adjacent to an external surface of the hybridization chamber. A desired temperature is maintained within the hybridization chamber by thermal exchange across a relatively thin wall of the hybridization chamber against which the temperature controller block is placed. The thickness of the wall is typically dependent upon a number of factors including, e.g., the composition of the material, the desired temperature range, manufacturing tolerances, and the like.

Controlling the temperature of the temperature control block may be carried out by a variety of means. For example, in preferred aspects, the temperature control block may be a thermoelectric temperature controller, e.g., a Peltier heater/cooler. Alternatively, the temperature control block may incorporate a series of channels through which is flowed a recirculating temperature controlled fluid, e.g., water, ethylene glycol or oil, which is heated or cooled to a desired temperature, e.g., in an attached water bath.

Alternatively, where hybridization temperatures are sufficiently above ambient temperatures, the temperature control block may be a thermostatically controlled heater block which operates to maintain the hybridization chamber at a static temperature. Thus, the temperature control block is activated, i.e., heating, when the temperature within or immediately adjacent the hybridization chamber is below the desired temperature, and inactive, i.e., not heating, when the temperature within the hybridization chamber is at or above the desired temperature.

The temperature control system may also include a temperature control element to preheat or precool the fluid prior to injection into the hybridization chamber. This additional temperature control may be supplied at a variety of places in the fluidics station. For example, the reagent/sample vessels may be placed in a temperature controlled environment, e.g., a water bath, to achieve optimal pre-injection temperatures. Alternatively, an in-line temperature controller may be employed to adjust the temperature of the fluid as it is being delivered to the hybridization chamber. Typically, this involves the use of a coiled heat-exchange tube as part of the fluid passage 210. The heat-exchange coil is generally disposed around a temperature controlled element and is fabricated from a material having a relatively high thermal transfer coefficient, e.g., stainless steel, copper, aluminum, etc.

E. Cartridge Mounting System

In order to perform the hybridization operations for which the fluidics station is designed, an array cartridge 100 is mounted upon the fluidics station such that it is maintained in fluid communication with the fluid delivery system, and subject to the other operations of the fluidics station, e.g., temperature control, mixing, etc. To accomplish this, the mounting system typically immobilizes and aligns the array cartridge so that it may be fluidically connected to the fluid delivery and other systems.

Figure 3A:
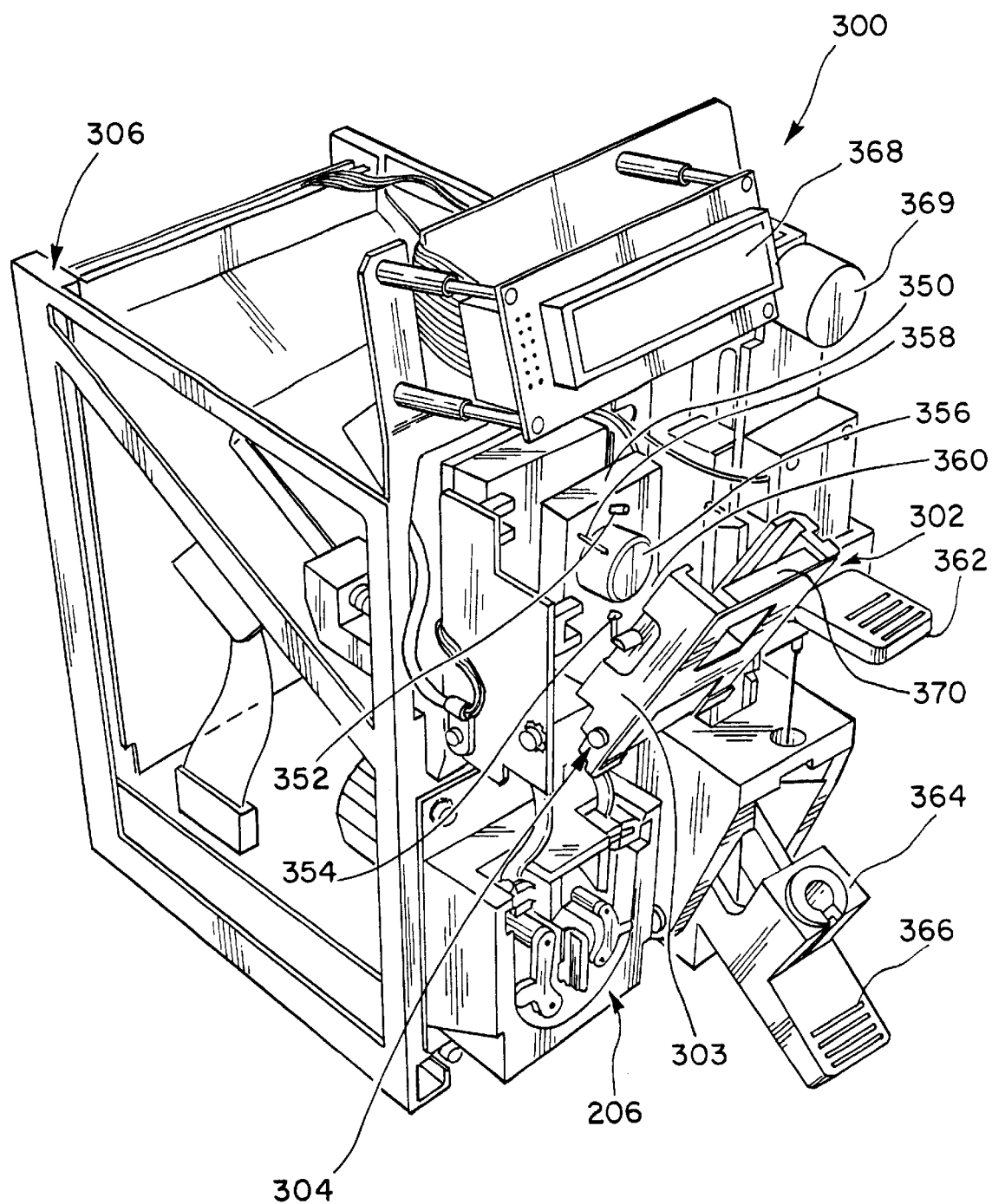
FIG. 3A is an illustration of one embodiment of a single fluidics module for inclusion in a fluidics station of the invention. The module is shown detached from the fluidics station as a whole and without external covering.
Figure 3B:
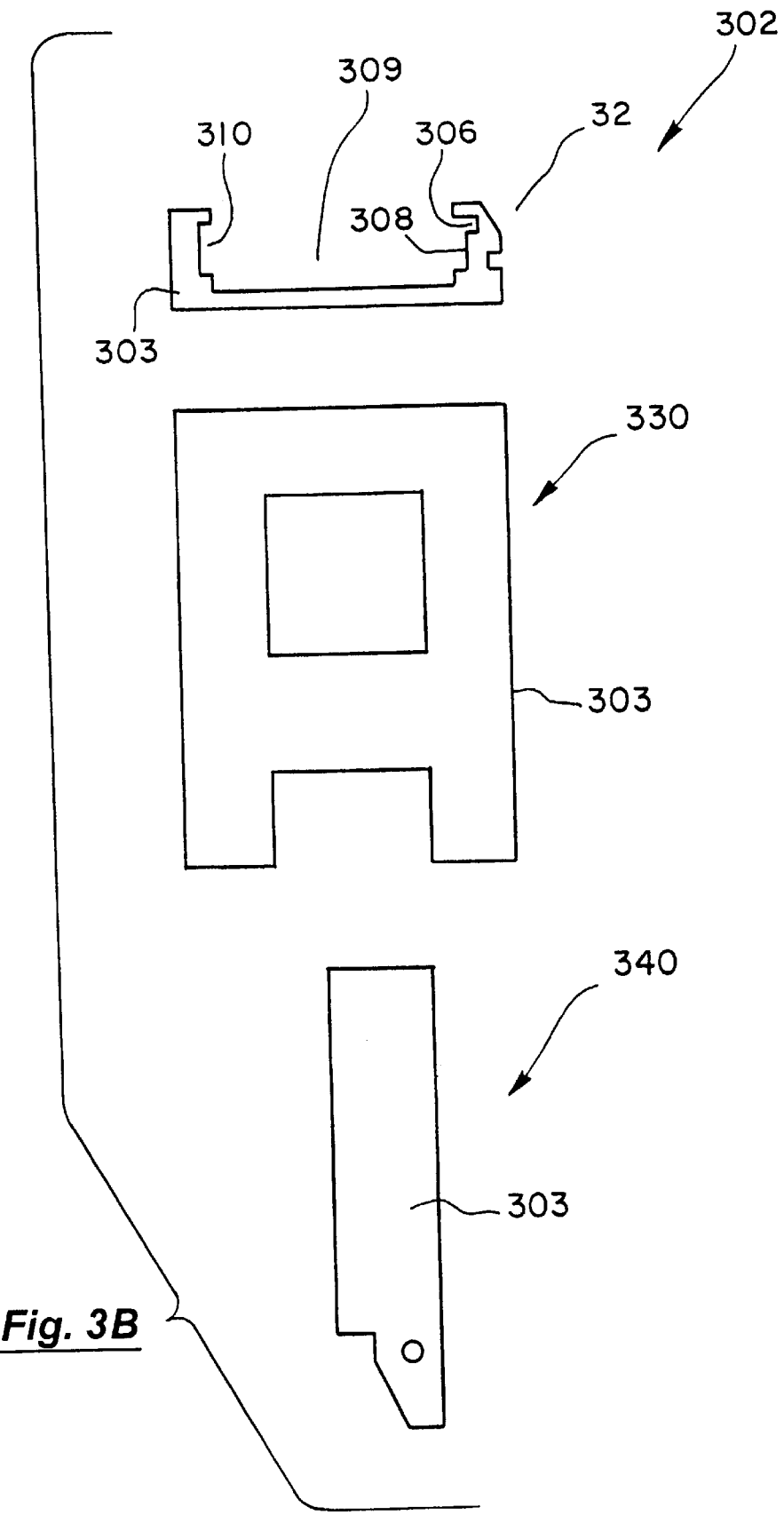
FIG. 3B is a detailed schematic illustration of one embodiment of a mounting frame for inclusion in the fluidics station of the invention from the end, back and side view.
Figure 3C:
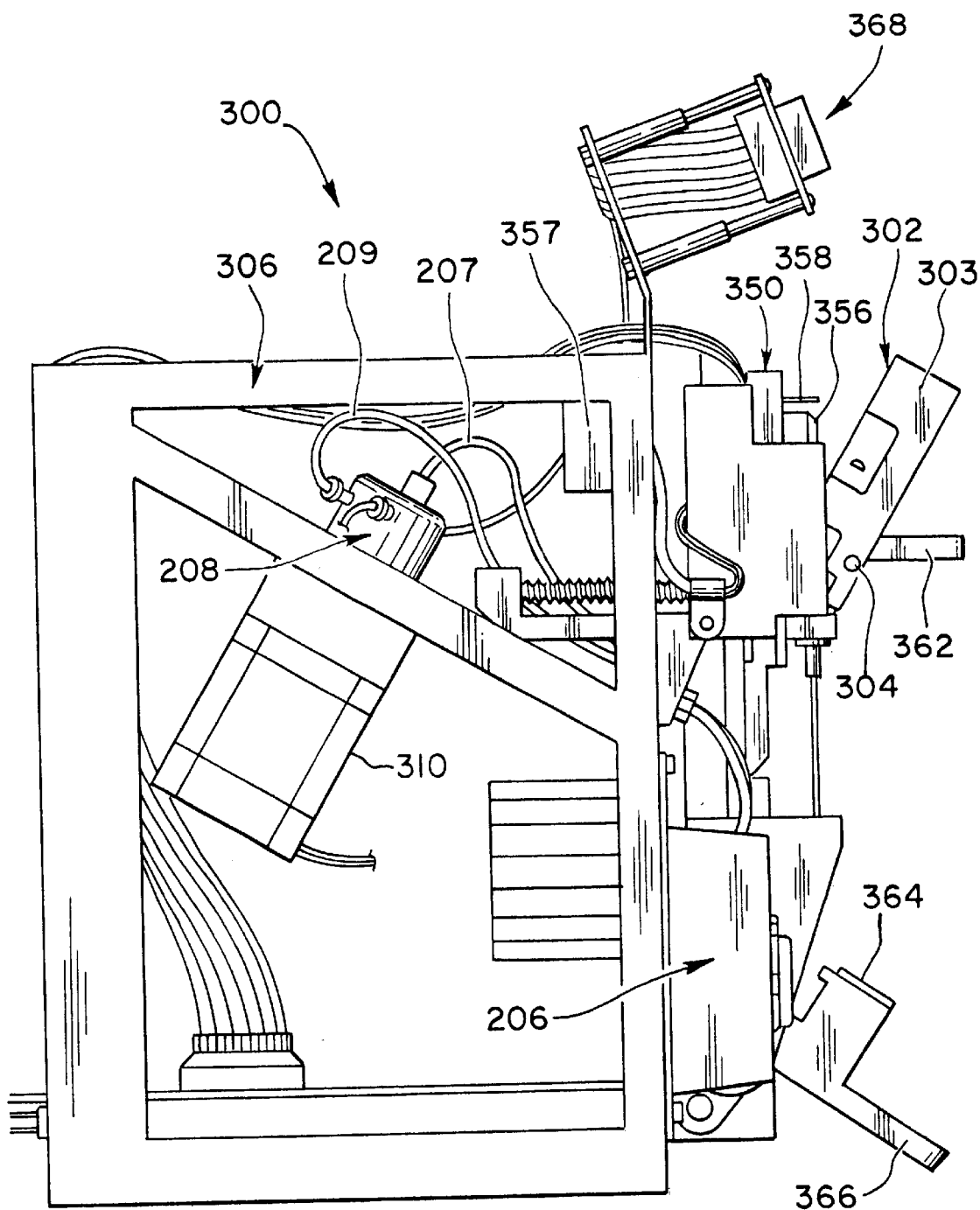
FIG. 3C is a side view of the fluidics module of FIG. 3A.

A representative cartridge mounting system is shown in FIGS. 3A and 3C which depicts a single hybridization module 300. Each hybridization module 300 includes a frame 306 and a mounting system 302 coupled to the front of frame 306 for mounting an array cartridge 100 thereon. Each module 300 preferably operates independently from the other modules in the fluidics station. Thus, each module 300 preferably includes a fluid distribution system 200 as described above, and the appropriate drive motors and electronics for operating the fluid distribution system 200 (discussed below). As shown in FIG. 3C, a module 300 includes a pump 206, which is preferably a peristaltic pump, coupled to a valve assembly 208 via first port 207. Valve assembly 208 is connected to a plurality of reagent vessels via tubes 204, and 224–228 (see FIG. 2), and to array cartridge 100 via port 209. Valve assembly 208 includes a drive motor 310 for opening and closing the different ports of valve assembly 208 to selectively couple the hybridization chamber to one of the reagent vessels or to the waste vessel (as discussed above).

As described above, the array cartridge 100 typically includes a number of alignment structures to ensure correct alignment of the array during the various operations involved in hybridization and detection of ligands that hybridize to an array. Accordingly, the mounting system will typically include one or more alignment structures that are complementary to those structures on the cartridge. For example, one such mounting system is system 302 illustrated in FIG. 3A. As shown, mounting system 302 includes a mounting frame 303 and mounting plate 350. Mounting frame 302 is shown in greater detail in FIG. 3B and is generally adapted to fit the array cartridge. Shown are three views of the mounting system 302 from the end view 320, back view 330 and side view 340. As shown in FIG. 3B, frame 303 of mounting system 302 includes a slot 309 into which the array cartridge may be inserted. The slot has a series of grooves 306–310 in its sides which hold the array cartridge in position. Groove 306 is included to receive a non-flush edge of the cartridge and thereby ensure insertion of the array cartridge into the mounting frame in the appropriate orientation. The mounting frame may also include a shunt or "wash block" 370 (see FIG. 3A) built into the mounting frame, also termed a "fluid bypass" for flowing fluid between the two injection needles 358 and 360 in the absence of a cartridge in the device. Optionally, wash block 370 may be removable so that it may be discarded after a cleaning process.

The mounting system 302, shown in greater detail in FIG. 3B, is typically connected to the mounting plate 350 in the fluidics station by way of a hinge 304. In this embodiment, the mounting frame is similar to a door on an audio cassette player. Once the array cartridge 100 is inserted into the mounting frame 303, the frame is closed so that the array cartridge is placed up against the mounting plate 350. A variety of other methods may be used to couple the mounting frame to the mounting plate, e.g., clips, screws, latches, etc.

As with the mounting frame 303, the mounting plate 350 may be similarly designed to be complementary to the structure of the array cartridge. For example, as shown in FIG. 3A, the mounting plate 350 may optionally include alignment structures, such as mounting pins 352 and 354. As previously described, in one preferable embodiment, pins 352 and 354 are not employed, with mounting frame 303 providing the necessary alignment. In addition, the mounting plate may also include a number of the control/fluid delivery aspects of the fluidics station. For example, as shown in FIG. 3A, the mounting plate includes a temperature controller/monitor assembly and injection needles 358 and 360. As described in detail above, the temperature controller/monitor assembly preferably includes a temperature controller/monitor block 356 extending from mounting plate 350 for directly contacting an external surface of the hybridization chamber. A heater/cooler 357 (FIG. 3C) is coupled to block 356 for heating/cooling the block and maintained the desired temperature within the hybridization chamber by thermal exchange.

As shown, the temperature controller block and injection needles are complementary to the array cartridge shown in FIG. 1. Accordingly, when an array cartridge is mounted upon the mounting plate, the external surface of the array cartridge 100 adjacent the hybridization chamber is placed against the temperature controller block 356. The temperature controller block 356 is coupled to a thermoelectric temperature controller that maintains the desired temperature within the hybridization chamber by thermal exchange across a relatively thin wall of the array cartridge.

The injection needles 358, 360 are inserted into the inlet/outlets 130, 134 on the array cartridge, with frame 303 providing the necessary alignment. In alternate aspects, the needles may be retractable so that they may be inserted into the inlets/outlets, as desired, following mounting of the array cartridge on the fluidics station between the sample and the cartridge. For example, in the embodiment shown in FIG. 3A, the injection needles are not actually inserted into the inlet and outlet of the cartridge until lever 362 is raised, which moves the mounting plate 350 and injection needles 358, 360 into contact with the cartridge. Additional levers may be provided to facilitate addition and removal of sample vials from the device, e.g., lever 366. Optionally, one or more sensors, such as optical sensors, may be provided to sense when the vial is in place and when sample tube 204 has been placed in the vial. One or more sensors may also be provided to determine if the entire system is closed and a cartridge is in place.

Figure 3D:
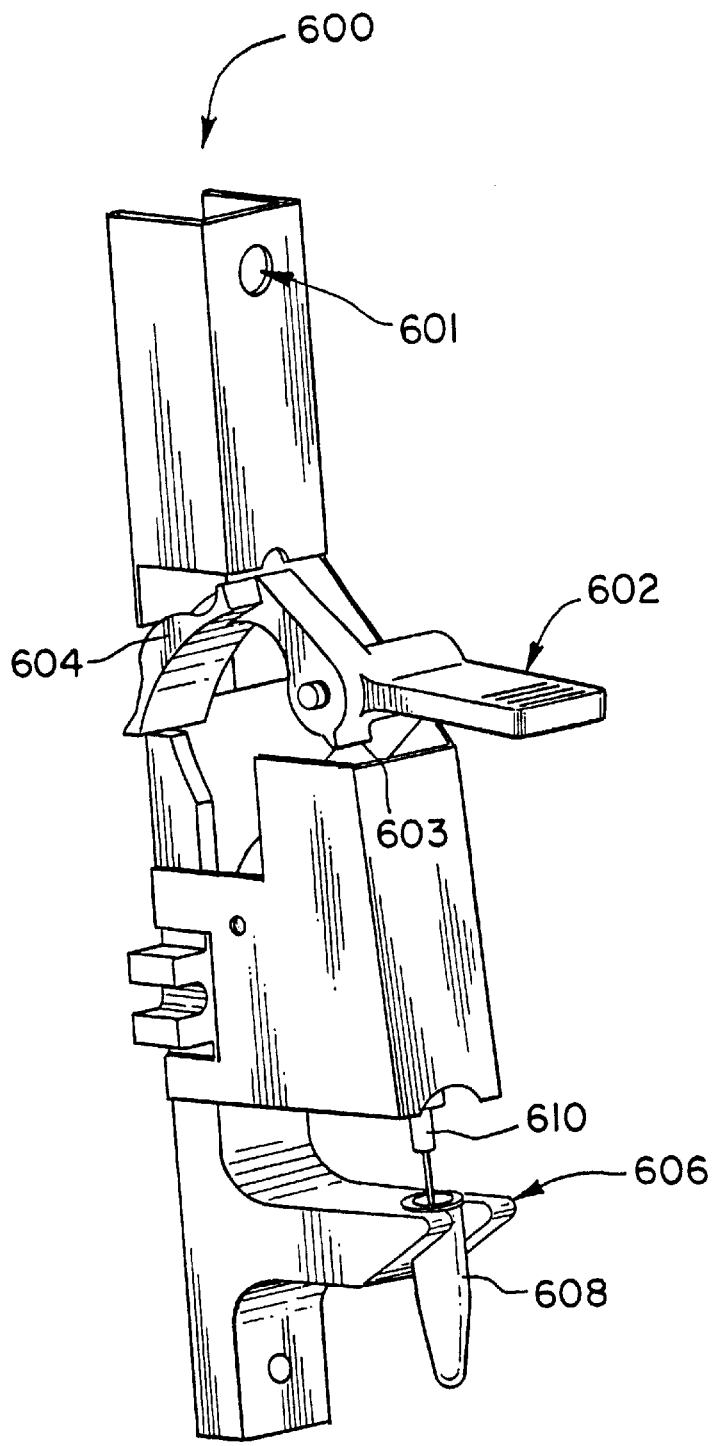
FIG. 3D is a perspective view of an alternative system for loading and unloading a cartridge according to the invention.

FIG. 3D illustrates an alternative system 600 for coupling array cartridge 100 to injection needles 358, 360 (see FIG. 3A). System 600 may conveniently be coupled to the fluidics station of FIG. 3A by placing input control 369 through a hole 601 and then mounting system 600 vertically on the front of the fluidics station.

System 600 includes a lever 602 which is shown in a "ready state" where a cartridge is ready to be loaded into mounting frame 303. Lever 602 has a cam 603 and a curved section 604 which also acts as a camming surface. In this way, cams 603 and 604 serve to close mounting frame 303 or to allow mounting plate 350 to slide forward depending on whether lever 602 is raised or lowered. More specifically, depression of lever 602 (approximately 5 degrees) causes cam 603 to move downward, releasing a lever which holds mounting frame 303 closed. Upon release of the lever, mounting frame 303 opens to allow a cartridge to be inserted. Mounting frame 303 is then manually closed and lever 602 is raised (approximately 30 degrees) to move cam 604. In turn a cam follower (not shown) slides forward, allowing mounting plate 350 to also slide forward and engage the cartridge (or the wash block) as described herein.

System 600 further includes a yoke member 606 which is configured to hold a sample vial 608. Disposed above yoke member 606 is a needle assembly 610 which draws the sample from vial 608 in a manner similar to that described herein. When vial 608 is inserted over needle assembly 610 and raised upward, a switch (not shown) senses the movement of needle assembly 610 to indicate to the fluidics station that the vial is in place.

Figure 7A:
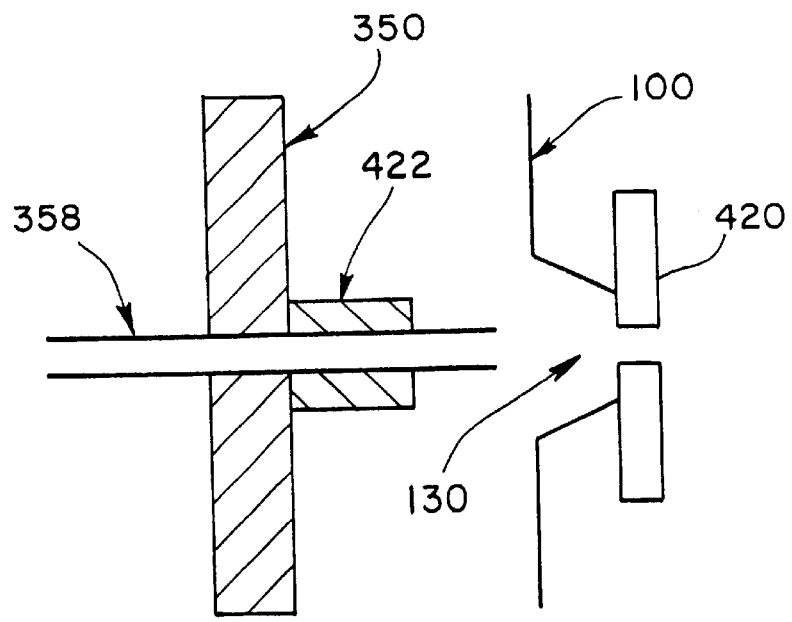
FIGS. 7A and 7B are schematic illustrations of the method for inserting an injection needle into one of the ports of the polymer array cartridge device.
Figure 7B:
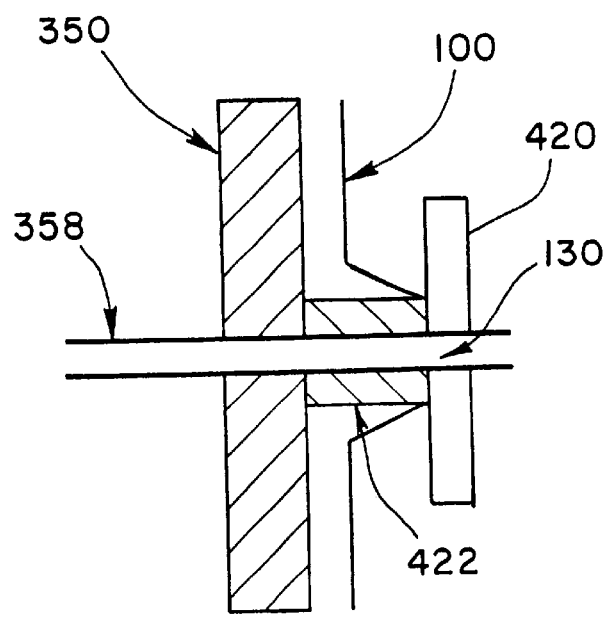

FIG. 7A and 7B schematically illustrate the insertion of one of the injection needles 358 of mounting plate 350 into one of the inlet and outlet ports 130, 134 of array cartridge 100. As shown, inlet port 130 includes a septum 420 for sealing port 130 when needle 358 is inserted therein (see FIG. 7B). In one embodiment, mounting plate 350 may optionally include a collar 422 attached to the exterior of plate 350 and sized to fit around needle 358; however, in the preferred embodiment, collar 422 is not employed. Collar 422 is slightly compressed by the cartridge tube around port 130 when needle 258 is inserted therein (see FIG. 7B). This provides an additional seal between the cartridge 100 and mounting plate 350. Compression tube is preferably fabricated from injection molded plastic parts, and will have a length selected to be long enough to reach the septum 420 without compromising the seal.

Figure 4:
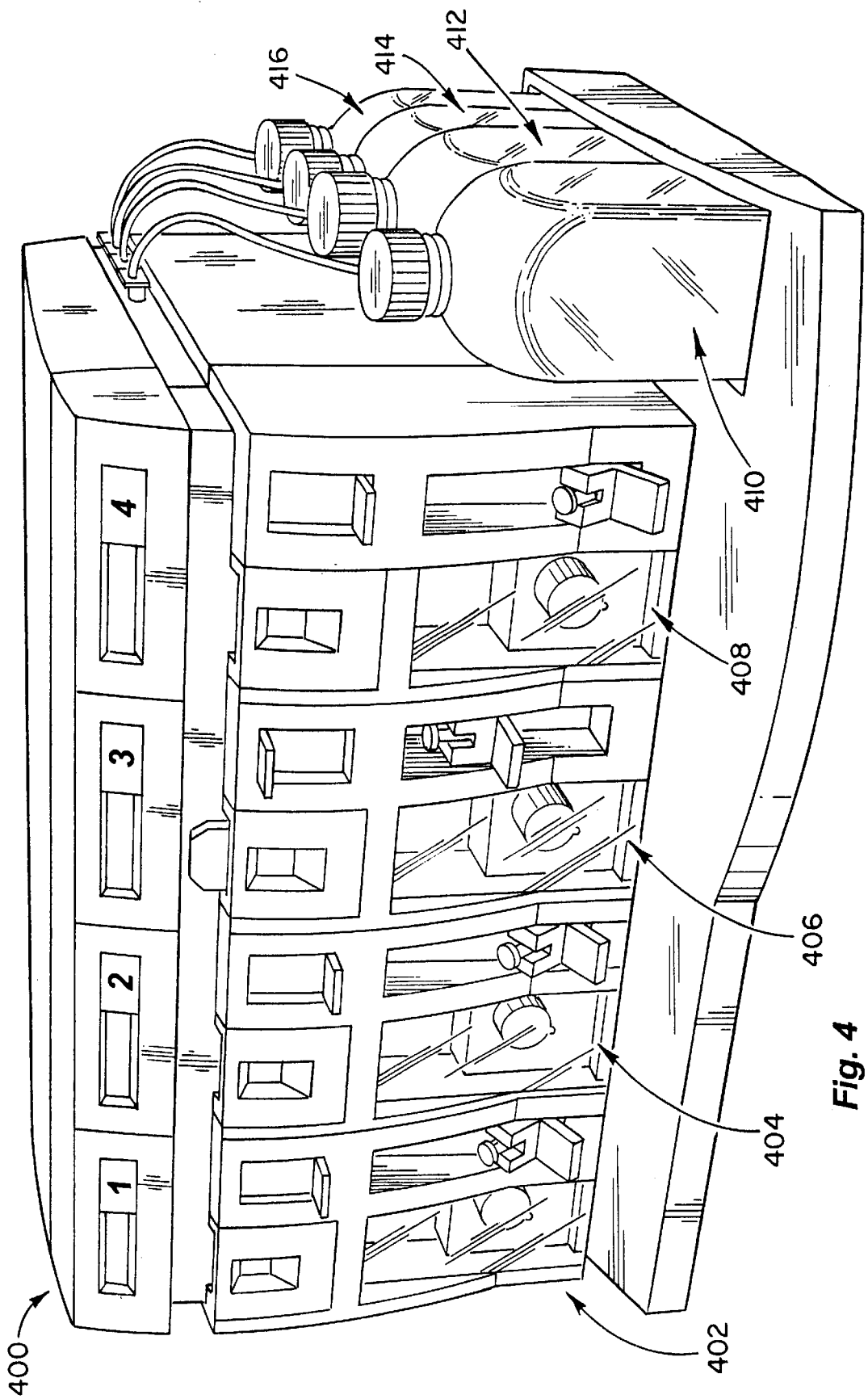
FIG. 4 shows an illustration of one embodiment of a fully assembled fluidics station of the invention.

As shown in FIGS. 3A and 4, each module also may optionally include an LCD readout 368 for monitoring the various conditions of a given hybridization, or the status of a given reaction protocol. An input control 369 may also be provided for adjusting the contrast of readout 368.

A fully assembled fluidics station 400 including four separate modules 402, 404, 406, 408 is shown in FIG. 4. The third module 406 is illustrated with a cartridge 100 inserted. Each module operates independently from the other modules, and includes its own processor/controller (not shown) and fluid delivery system (see FIG. 2). The fluid delivery systems of all the modules are coupled to common fluid sources and/or waste locations, which may include a waste bottle 410, a water bottle 412, and separate wash bottles 414, 416. The fluid sources or waste locations each have a separate fluid tube that extends into fluidics station 400, and independently couples to the valves of the separate modules.

F. Process Control System

The fluidics stations of the present invention also typically include process control systems for automatically carrying out the various steps involved in performing the desired reaction, e.g., hybridization. The process control system typically monitors and controls the fluid delivery system, the mixing system and the temperature control system according to a preprogrammed set of instructions. This generally involves delivering sample and/or wash fluids to the hybridization chamber at selected times during a hybridization operation or "run", mixing the fluids within the hybridization chamber at selected times, and controlling the temperature of the hybridization chamber according to a selected temperature profile.

Process control is generally carried out by an onboard processor contained within the fluidics station itself. The onboard processor is typically appropriately programmed to operate the above described systems according to an input set of process parameters. Specifically, the processor operates to provide appropriate instructions to each of the elements of the fluidics station according to a preselected time/temperature/mixing profile selected by the user, e.g., pump or valve operation, temperature sensor/controller operation, etc. Examples of programming to accomplish these objectives are shown in Appendix A. In some aspects, the fluidics station may include a keypad for direct entry of the desired profile into the on-board processor. The process parameters may alternatively be input by the user into a computer that is connected to the on-board processor, e.g., an IBM compatible PC, Macintosh or the like. The computer will typically be programmed with appropriate script programs for input of these various process parameters. An example of script programming is shown in the attached Appendix B. In this configuration, the fluidics station functions as a slave to the master computer. The computer transmits the parameters entered in the script program to the on-board "slave"processor on the fluidics station which functions as described above. As provided, the control software operates generally as follows:

A hybridization script comprises a sequence of hybridization commands each terminated by an ASCII Null character ('\0' in the C language). Hybridization commands are, in turn, strings of printable ASCII characters, the first of which is the command code and the remainder of which constitute the command parameters, if any. When a module in the fluidics station is directed by the master control element, e.g., a control computer, to begin the execution of a script, it starts with the first command and continues in sequence unless it encounters a command that changes the sequence of execution (such as the Call command). Execution stops when the last command in the script is executed, when an End command is executed, or when certain error conditions are detected. In the latter case the execution of the script is said to have terminated abnormally, and the master can determine what caused the abnormal termination by asking for the script status.

Subroutines are allowed in a hybridization script. They are defined before they are called. In the particular embodiment shown in Appendix A, up to sixteen subroutines are allowed, but no subroutine may be defined within the context of another. Subroutines may call other subroutines, but to no greater depth than sixteen levels. The last command of each subroutine is a Return command, and there may be no other Return commands within the subroutine.

At the option of the user, a given hybridization script may pass through a number of different "stages" each of which terminates after a specified amount of time or upon the occurrence of a certain event. The fluidics station provides two commands relating to stages, one to enter a stage and, optionally, to start a timer for it, and the other to wait for the stage to be completed. Each stage is identified by a character that is one of the parameters of the Enter Stage command; that character has no particular meaning to the fluidics station, but the master can determine what stage a given script is in and how soon the stage will end (if it is a timed stage) by asking for a status report on the script.

Some hybridization commands are executed in immediate mode, i.e., they interact directly with the hardware of the fluidics station and do not require long times for execution or have script-management functions. For debugging purposes it is convenient to be able to execute commands of this type directly from the master, so the ability to do that is built into the fluidics station. Commands that can be executed in this "immediate mode" are so identified in the descriptions below.

Each module of the fluidics station can include an LCD, e.g., with two lines of sixteen characters each. The LCD is able to display the entire ASCII character set plus a set of special characters whose codes have their most significant bits set, e.g., (·), whose code is OXDF. Each character position has an address associated with it. Reading from left to right, the character positions of the top line are at addresses 0 through 15, and those of the bottom line are at 64 through 79. The controller for the LCD has an address pointer that determines where the next character written will go, and there is a hybridization command that sets the address pointer. Once the pointer has been set, writing a character to the LCD causes the pointer to be incremented.

As shown in the software provided in the attached appendices, all hybridization commands use the same basic format: the first character is the code for the command, and the remaining characters, if any, convey the values of one or more parameters. To simplify parsing of the commands, all parameters except possibly the last one are usually of fixed length so that no separators are required. Parameters that have units of measure associated with them, such as time or temperature values, are expressed in units that allow them to have whole-number values at the resolution supported by the fluidics station so that a floating-point package is not needed.

The hybridization commands currently supported by the fluidics station are described below, with the ones that can be executed in immediate mode listed first:

The "Clear LCD" (command code 'C') command causes the LCD on the module to be cleared to blanks and the address pointer to be set to 0. It may be executed in immediate mode. This command is rejected if its length is greater than one character. If it is executed from a hybridization script under those circumstances, execution of the script terminates in the Bad Command state.

The "Clear LCD Field" (command code 'F') command causes a field on the LCD to be cleared to blanks. The field begins at the character position addressed by the current value of the address pointer and has a length specified by the command parameter. The address pointer is not altered by execution of the command. The command may be executed in immediate mode. This command takes one parameter, the field length expressed as a whole number in a string of ASCII digits. The length of the string is variable. If the value of the parameter exceeds the length of a line on the LCD, then it is treated as if equal to the line length. This command is rejected if its parameter is missing. If it is executed from a hybridization script under those circumstances, execution of the script terminates in the Bad Command state.

The "Go To LCD Address" (command code 'G') command changes the address pointer in the LCD to the value of the command parameter. It may be executed in immediate mode. This command takes one parameter, the desired address expressed as a whole number in a string of ASCII digits. The length of the string is variable. The address should be in the range from 0 to 127, but if it is not, the value written to the address pointer is the parameter modulo 128. This command is rejected if its parameter is missing. If it is executed from a hybridization script under those circumstances, execution of the script terminates in the Bad Command state.

The "Write to LCD" (command code 'W') command causes its parameter to be written to the LCD starting at the position specified by the LCD's address pointer. The LCD's address pointer is left pointing to the character position to the immediate right of the last character of the string. The command may be executed in immediate mode. The parameter may contain blanks. This command takes one parameter, the ASCII string to be written to the LCD. This command is rejected if its parameter is missing. If it is executed from a hybridization script under those circumstances, execution of the script terminates in the Bad Command state.

The "Set DAC" (command code 'S') command causes its parameter to be written to the digital-to-analog converter (DAC) in the fluidics station, which is an eight-bit device. It may be executed in immediate mode. This command takes one parameter, a value to be written to the DAC expressed as a whole number in a string of ASCII digits. The length of the string is variable. Valid values range from 0 to 255, with 0 corresponding to a DAC output of 0 volts, and 255 corresponding to an output of 5 volts times 255/256. If the parameter has a value outside the valid range, the value sent to the DAC is the parameter modulo 256. This command is rejected if its parameter is missing. If it is executed from a hybridization script under those circumstances, execution of the script terminates in the Bad Command state.

The "Set Temperature" (command code 'T') command establishes the temperature to which the temperature control system in the module will attempt to drive the cartridge. It may be executed in immediate mode. This command takes one parameter, the desired temperature expressed in tenths of a degree C and encoded as a whole number in a string of ASCII digits. The length of the string is variable. Valid values range from 150 to 500, corresponding to a temperature span from 15° C. to 50° C. This command is rejected if its parameter is missing or outside the valid range. If it is executed from a hybridization script under those circumstances, execution of the script terminates in the Bad Command state.

The "Move Motor" (command code 'M') command causes the fluidics station to move one of its motors (the valve motor or the pump motor) in the manner specified by the command parameters. It is intended primarily for debugging, and care should be taken in using it to avoid conflicts with other parts of the firmware. This command may be executed in immediate mode. The first parameter of this command is a single character specifying the motor to be moved. A character whose ASCII code is even (e. g., '0') specifies the peristaltic pump motor, and a parameter whose ASCII code is odd (e. g., '1') specifies the valve motor. The second parameter is a single upper-case letter specifying the ramp table to be used for the motion, selected from a set of preset ramp tables. The third parameter is a single character in the range from '0' to '?' that specifies which sensors, if any, are to be watched during the motion to decide whether to terminate it before the specified number of steps have been taken. Only the lower four bits of the code for the character are significant. In the case of the valve the significant sensors are the outer valve encoder (selected by bit 0 of the mask) and the inner valve encoder (selected by bit 1 of the mask). Thus, a value of '0' for the parameter specifies that no sensors are watched, '1' specifies that only the outer valve encoder is watched, '2' specifies that only the inner valve encoder is watched, and '3' specifies that both are watched. In the case of the peristaltic pump, the upper (selected by bit 0 of the mask) and lower (selected by bit 1 of the mask) fluid sensors are the significant ones. The fourth parameter is a single character in the range from '0' to '?' that specifies the pattern the sensors selected by the sensor mask must assume to cause the motor motion to terminate before the requested number of steps have been taken. A. "0" in a particular bit position specifies that the corresponding sensor is to be on, and a "1" specifies that it is to be off. Thus, for example, if the parameter has the value '1' and the valve motor is the one that is to be set into motion, then the valve will be stopped if the outer valve encoder is off and the inner one is on. Note that corresponding bits in the sensor pattern and sensor mask apply to the same sensor. The count mask parameter is a single character not currently used. The "Step count" parameter is a variable-length string of ASCII digits giving the number of steps the motor should take during the motion. A positive value specifies clockwise rotation, and a negative value specifies counter-clockwise rotation. The absolute value of the parameter must equal or exceed the minimum value supported by the specified ramp table and it must not exceed the largest value that can be expressed in an integer (32,767). * If the ramp selector does not specify a supported ramp, if the step count is out of range, or if not all the parameters are present, the "Move Motor" command is rejected, and if it is rejected during the execution of a hybridization script, execution of the script terminates in the Bad Command state.

The "Pump" (command code 'P') command causes the fluidics station to run the peristaltic pump in the manner specified by the command parameters. The movement will stop after a specified number of steps have been made or, optionally, after a particular pattern of fluid sensor states has been observed. The speed at which the pump moves is specified by the command. This command may be executed in immediate mode. The first parameter is a single upper-case letter specifying the ramp table to be used for the motion. The second parameter is a single character in the range from '0' to '?' whose lower four bits are used to determine which of the fluid sensors are used to stop the pump motion, if any. At present, only two fluid sensors are implemented, so the four useful values of this parameter are these: '0' to specify that no sensors are to be used, '1' to specify the upper fluid sensor, '2' to specify the lower fluid sensor, and '3' to specify both sensors. The third parameter is a single character in the range from '0' to '?' whose lower four bits are used to specify the state of the sensors selected by the sensor mask that will be used to stop the pump motion. For example, if the sensor mask is '3' and it is desired to stop the motion when the lower fluid sensor is on (0) and the upper fluid sensor is off (1), the sensor target should be '1'. If the motion is not to be stopped by any sensor pattern, the sensor mask should be set to '0' and the sensor target should be set to anything but '0'. The "step count" parameter is a variable-length string of ASCII digits giving the number of steps the motor should take during the motion. A positive value specifies clockwise rotation, and a negative value specifies counter-clockwise rotation. The absolute value of the parameter must equal or exceed the minimum value supported by the specified ramp table and it may not exceed the largest value that can be expressed in an integer (32,767). One revolution of the pump head, which corresponds to 1200 steps, moves approximately 0.25 ml. of fluid.

Again, if the ramp selector does not specify a supported ramp, if the step count is out of range, or if not all the parameters are present, the "Pump" command is rejected, and if it is rejected during the execution of a hybridization script, execution of the script terminates in the Bad Command state. Additionally, if the valve has not been homed or has not operated correctly since it was last homed, this command is rejected. If it is encountered during the execution of a hybridization script under those circumstances, execution of the script terminates in the Valve Homing Error state.

The "Stop Pump" (command code 'X') command causes the fluidics station to stop any motion of the peristaltic pump that may be in progress when the command is executed. The pump motor will be properly decelerated as it is stopped, so it may move by several steps before coming to rest. This command may be executed in immediate mode. This command is rejected if its length is greater than one character. If it is executed from a hybridization script under those circumstances, execution of the script terminates in the Bad Command state.

The "Await Sensors" (command code 'a') command causes the fluidics station to wait until either a specified pattern of sensor states is detected or a timeout occurs. The debounce algorithm is used to determine whether the sensor pattern has legitimately occurred. It works as follows. When the Await Sensors command is first encountered, a task is started to observe the sensors once every debounce interval. If that task observes the specified sensor pattern for n consecutive debounce intervals, where n is the debounce count, then the pattern is judged to have legitimately occurred. See the Debounce Count and Debounce Interval commands. This command takes two parameters. The first is a variable-length string of characters each in the range from 'A' to 'P' or from 'a' to 'p' that specifies the sensor pattern. Each upper-case letter in the string identifies a sensor that must be on to match the pattern, and each lower-case letter identifies a sensor that must be off. Sensors not identified may be in either state to match the pattern. It is not an error to identify a sensor more than once, but if at least one of the identifying letters is lower-case, then the sensor will have to be off to match the pattern. Only the first sixteen characters in the string are significant. The second parameter, which begins at the first decimal digit encountered as the fluidics station is decoding the command, is the desired timeout interval expressed in tenths of a second and encoded as a whole number in a string of ASCII digits. The length of the string is variable. Valid values range from 1 to 863999 (that is, just less than twenty-four hours).

If any character within the first command parameter is outside the range defined above or if the second parameter is out of range, execution of the hybridization script terminates in the Bad Command state. Note that the fluidics station treats the first decimal digit it encounters as it reads the command as the beginning of the second parameter. Additionally, if the given sensor pattern is not observed (within the meaning of the debounce algorithm) at any time within the specified timeout interval, execution of the hybridization script terminates in the Sensor Timeout state. Note that if the command identifies no sensors to be part of the pattern to be matched, the timeout will never occur.

If the hybridization script is in a timed stage, the "await Stage End" (command code 'n') command causes the fluidics station to wait until the stage is over; that is, until the timer set by the Enter Stage command reaches 0. Otherwise, there is no waiting. If the length of this command is more than one character, execution of the hybridization script terminates in the Bad Command state.

The "Await Temperature" (command code 't') command causes the fluidics station to wait until either the temperature of the chip comes within 0.3° C. of the most recently specified setpoint or a timeout occurs. This command takes one parameter, the desired timeout interval expressed in tenths of a second and encoded as a whole number in a string of ASCII digits. The length of the string is variable. Valid values range from 1 to 863999 (i.e., just less than twenty-four hours). If the parameter of this command is outside the valid range, execution of the hybridization script terminates in the Bad Command state. Further, if the temperature of the chip does not meet the criterion defined above within the specified timeout interval, execution of the hybridization script terminates in the Temperature Timeout state.

The "Break" (command code '!') command causes the subroutine or loop within which it is executed to be terminated immediately. In the case of a subroutine, it does so by causing the commands following it to be skipped until the Return command is encountered. In the case of a loop, it acts by causing the commands following it to be skipped until an Until Count or Until Stage Time command is encountered, at which point it forces the command to be executed in a way that terminates the loop. If a Break command is executed outside any loop or subroutine, it causes the termination of the entire script. If the length of this command is more than one character, execution of the hybridization script terminates in the Bad Command state.

When the fluidics station encounters the "Call Subroutine" (command code 'c') command, it pushes the location of the command after the call command onto a stack and then transfers control of the script to the subroutine named by the parameter of the command (see the Label Subroutine command). This command takes one parameter, a character in the range from 'A' to 'P' that gives the name of the subroutine to be called. If the parameter of this command is outside the valid range or refers to a subroutine for which an entry point has not already been defined by a Label Subroutine command, if there is no room on the stack for the location of the command after this Call Subroutine command, or if the number of characters in this command differs from two, execution of the hybridization script terminates in the Bad Command state.

The "Debounce Count" (command code 'b') command establishes the number of times the debounce algorithm needs to see a given sensor in the specified state before it accepts the sensor state as valid. See the description of the Await Sensors command, above. Once a debounce count is set, it applies to all Await Sensors commands until a new value is set. The default value for the debounce count established when execution of a hybridization script is started is 1. This command takes one parameter, the debounce count encoded as a whole number in a string of ASCII digits. The length of the string is variable. Valid values range from 1 to 32767. If the parameter of this command is missing or out of range, execution of the hybridization script terminates in the Bad Command state.

The "Debounce Interval" (command code 'i') command establishes the amount of time the debounce algorithm waits between successive tests of the sensor. See the description of the Await Sensor On and Await Sensor Off commands, above. Once a debounce interval is set, it applies to all Await Sensor On and Await Sensor Off commands until a new value is set. The default value for the debounce interval established when execution of a hybridization script is started is 25 milliseconds. This command takes one parameter, the debounce interval in milliseconds, encoded as a whole number in a string of ASCII digits. The length of the string is variable. Valid values range from 1 to 1000. If the value is less than the size of one tick of the real-time clock in the fluidics station (currently 5 milliseconds), then it is treated as equal to the size of one tick. If the parameter of this command is missing or out of range, execution of the hybridization script terminates in the Bad Command state.

The "Do" (command code 'd') command marks the beginning of a loop (see Until Count and Until Stage Time commands). If the command code for this command is followed by any character other than an ASCII Null, execution of the hybridization script terminates in the Bad Command state. As provided in the appended software, loops may be nested to a depth of four. If this command is encountered after that depth has already been reached, execution of the hybridization script terminates in the Bad Command state. Note that if a subroutine with a loop in it is called from within a loop, two levels of nesting are used.

The "End" (command code 'x') command causes immediate termination of the hybridization script.

The "Enter Stage (command code 'e') command causes the fluidics station to record its first parameter in a place that the master can access to determine what stage the hybridization script is occupying and optionally to start a timer to time the duration of the stage. This command takes two parameters. The first is a single character of any desired value except ASCII null to be used to identify the stage to the master. The second is the desired timeout interval expressed in tenths of a second and encoded as a whole number in a string of ASCII digits. The length of the string is variable. Valid values range from 0 to 863999 (that is, just less than twenty-four hours), with 0 being a reserved value that indicates that the given stage is not a timed stage. If either parameter of this command is outside the valid range, execution of the hybridization script terminates in the Bad Command state.

The "Home Valve" (command code 'h') command causes the fluidics station to move the distribution valve to its home position (A) and to note that the valve has been homed. The motion is done in such a way that the valve enters the home position while moving clockwise. If the command code for this command is followed by any character other than an ASCII Null, execution of the hybridization script terminates in the Bad Command state. Further, if the valve sensors do not confirm that the valve has executed the homing sequence correctly, the script terminates in the Valve Homing Error state, and the valve is subsequently regarded as unhomed.

When the fluidics station encounters the "Label Subroutine" (command code 'l') command, it examines the command parameter. If that parameter is a valid subroutine name, it records the position of the next command in the script as the entry point of the subroutine, and then it bypasses commands in the script until it encounters and bypasses a Return command, at which point it resumes normal script execution. This command takes one parameter, a character in the range from 'A' to 'P' that gives the name of the subroutine being labeled. If the parameter of this command is outside the valid range or is the same as that of another Label Subroutine command encountered earlier in the same script, if the fluidics station is unable to find a Return command to mark the end of the subroutine, or if the number of characters in this command differs from two, execution of the hybridization script terminates in the Bad Command state.

If the fluidics station is executing a subroutine in a hybridization script and encounters the "Return" (command code 'r') command, it pops the top entry off the subroutine stack and uses it to find the next command to execute (which is, necessarily, the command after the one that called the subroutine). If the command code for this command is followed by any character other than an ASCII Null or if the command is encountered outside the context of a subroutine, execution of the hybridization script terminates in the Bad Command state.

The "Show Loop Counter" (command code 's') command writes onto the LCD, at the position addressed by the current value of the address pointer, a string of the form "AX of Y", where X is the current value of the loop counter for the innermost loop in which this command is embedded, and Y is the parameter of the Until Count command at the end of the loop.

If the command is not embedded in a loop, nothing is written to the LCD. The LCD, or at least the area where this command will write its string, should be cleared, and the address pointer of the LCD should be set, before this command is executed. If the command code for this command is followed by any character other than an ASCII Null, execution of the hybridization script terminates in the Bad Command state.

The "Show Stage Time" (command code 'y') command causes the fluidics station to begin writing the current value of the stage timer onto the LCD once per second until the stage is over. The position where the time is written is specified by the command parameter. The time is written right-justified in a field of five characters. If the fluidics station is not in the middle of a timed stage when this command is executed, the command does nothing. When the timed stage ends, the command writes 0 for the time and then discontinues updating the display. This command takes one parameter, a whole number encoded in a string of ASCII digits giving the address where the stage time is to be written onto the LCD. The length of the string is variable. The address should be in the range from 0 to 127, but if it is not, the value used for the address is the parameter modulo 128. If the parameter of this command is missing, execution of the hybridization script terminates in the Bad Command state.

The "Until Count" (command code 'u') command marks the end of a loop, and it arranges for the loop to be executed the number of times specified by its parameter. This command takes one parameter, the desired loop count encoded as a whole number in a string of ASCII digits. The length of the string is variable. If the loop count is zero or negative, the body of the loop is not executed. If the parameter of this command is missing or if the command is encountered without a preceding Do command, execution of the hybridization script terminates in the Bad Command state.

The "Until Stage Time" (command code 'z') command marks the end of a loop, and it arranges for the loop to be executed until the timer timing the current hybridization stage has been decremented to less than or equal to the command parameter. This command takes one parameter, the target stage time in tenths of a second, encoded as a whole number in a string of ASCII digits. The length of the string is variable. Valid values range from 0 to 863999 (that is, just less than twenty-four hours). If the parameter of this command is out of range, execution of the hybridization script terminates in the Bad Command state.

The "Valve" (command code 'v') command causes the fluidics station to move the distribution valve to the position specified by the command parameter. This command takes one parameter, the target valve position encoded as a signed integer in a string of ASCII digits. The length of the string is variable. Valid values for the magnitude of the parameter range from 1 (corresponding to valve position A) to 8 (corresponding to valve position H). A positive value causes the valve to move in the clockwise direction (from position A to position B to position C, and so on), and a negative value causes it to move the other way. If the parameter of this command is missing or outside the valid range, execution of the hybridization script terminates in the Bad Command state. If the valve has not been homed or has not operated correctly since it was last homed, execution of the hybridization script terminates in the Valve Homing Error state. The valve has a sensor that can be used to determine whether it has moved and whether it has reached the desired position. If the valve fails to reach the desired position, execution of the hybridization script terminates in the Valve Motion Error state, and the valve is afterwards regarded as unhomed until it is homed again.

The "Wait" (command code 'w') command causes the fluidics station to wait for the time interval specified by its parameter. This command takes one parameter, the desired timeout interval expressed in tenths of a second and encoded as a whole number in a string of ASCII digits. The length of the string is variable. Valid values range from 1 to 863999 (that is, just less than twenty-four hours). If the parameter of this command is outside the valid range, execution of the hybridization script terminates in the Bad Command state.

The "Wait For Motor" (command code 'm') command causes the fluidics station to wait for the motor motion that is in progress, if any, to be completed. For some values of the command parameter, it also causes the fluidics station to test the motor motion for certain error conditions. This command takes one parameter, a single character. If the parameter is '1', an error is recognized if the motor motion was not stopped by the detection of the sensor pattern specified in the command that started the motor. If the parameter is '2', '3', or '4' and the motor motion was not stopped by the detection of the sensor pattern, a counter is incremented (a different counter is used for each value of the parameter), and if the incremented value exceeds six, an error is recognized. The counter is cleared when a script is started and also whenever a Wait For Motor command with the same parameter is executed after a motor motion is started that is ultimately stopped by detection of the sensor pattern. Thus, the command must detect six consecutive failures of the motor motion to be stopped by the sensor pattern before an error is recognized, and there are three separate commands so that three separate motor motions can be monitored in overlapping fashion (the command is tailored specifically to monitoring the various phases of the drain-and-fill cycle). For all other values of the command parameter, the command waits for the motor motion to be completed, but generates no error. If the parameter of this command is missing or the command is not two characters long, execution of the hybridization script terminates in the Bad Command state. If the parameter of this command is '1' and if the motor does not stop until it has taken all the steps specified in the command that initiated its motion (that is, it does not stop because a specified sensor pattern was detected), then execution of the hybridization script terminates in the Motor Motion Error state. If the parameter of this command is '2', '3', or '4' and the conditions described above for the generation of an error are met, then execution of the hybridization script terminates in the Drain-and-Fill Error state.

The "If Sensors" (command code '{') command begins an If Sensors construct, which is a sequence of commands lying between an If Sensors and its matching End if and which may contain an optional Else command. The sequence of commands between the If Sensors and the Else (or the Endif, if the Else is absent) is the "True" branch of the construct, and the sequence of command between the Else, if present, and the matching Endif is the "False" branch. When the If Sensors command is encountered, a test is made to determine whether the sensor state specified by the command parameter matches the state of the sensors at the time when the command is executed. If so, the commands in the True branch are executed and the commands in the False branch, if present, are skipped. Otherwise, the commands in the True branch are skipped, and the commands in the False branch, if present, are executed. Certain rules are followed when nesting an If Sensors construct within another If Sensors or If Values construct, a subroutine, or a Do loop: (1) if any part of an If construct lies within the True branch of another such construct, then it all must lie there; (2) if any part of an If construct lies within the False branch of another such construct, then it all must lie there; (3) if any part of an If construct lies within a Do loop or subroutine, then it all must lie there; and (4) if any part of a Do loop lies within either branch of an If construct, then the entire loop must lie within that branch. The fluidics station firmware does not check for violations of those rules, but unexpected results will generally occur if they are not observed. This command takes one parameter, a variable-length string of characters each in the range from 'A' to 'P' or from 'a' to 'p' that specifies the sensor pattern. Each upper-case letter in the string identifies a sensor that must be on to match the pattern, and each lower-case letter identifies a sensor that must be off. Sensors not identified may be in either state to match the pattern. It is not an error to identify a sensor more than once, but if at least one of the identifying letters is lower-case, then the sensor will have to be off to match the pattern. If there are no letters in the parameter string, the True branch of the If Sensors construct will be unconditionally executed. If any character within the command parameter is outside the range defined above, or if there is no matching Else or Endif command following this command, execution of the hybridization script terminates in the Bad Command state.

The "If Value" (command code '[') command begins an If Value construct, which is a sequence of commands lying between an If Value and its matching Endif (see below) and which may contain an optional Else command. The sequence of commands between the If Value and the Else (or the Endif, if the Else is absent) is the "True" branch of the construct, and the sequence of command between the Else, if present, and the matching Endif is the "False" branch. When the If Value command is encountered, a test is made to determine whether the parameter of the command is non-zero. If so, the commands in the True branch are executed and the commands in the False branch, if present, are skipped. Otherwise, the commands in the True branch are skipped, and the commands in the False branch, if present, are executed.

The rules for nesting If Value constructs within other If constructs and loops are analogous to those for If Sensor constructs. This command takes one parameter, a whole number encoded in a string of ASCII digits. The length of the string is variable. Any value representable in integer format is valid. If the parameter of this command is missing, or if there is no matching Else or Endif command following this command, execution of the hybridization script terminates in the Bad Command state.

If the "Else" command (command code 'l') follows a matching If Sensors or If Value command (as it should), then it is not executed unless the True branch of the If Sensors or If Value construct was executed. In that case, it causes command execution to skip to the command after the matching Endif command so that no commands in the False branch are executed. If the command code for this command is followed by any character other than an ASCII Null, if there is no matching Endif command following this command, or if there was no matching If Sensors or If Value command executed prior to this command, execution of the hybridization script terminates in the Bad Command state.

If the "Endif" (command code '}') command follows a matching If Sensors or If Value command (as it should), then it marks the end of the If Sensors construct. This command take no parameters. If the command code for this command is followed by any character other than an ASCII Null or if there was no matching If Sensors or If Value command executed prior to this command, execution of the hybridization script terminates in the Bad Command state.

As provided in the appended software, a master computer provides the script to the on-board processor of the fluidics station. In particular, the fluidics station communicates with a host computer; e.g., a PC clone, over a network called the 9-Bit Solution, available from Cimetrics Technology. The network and its associated software represent an implementation of three levels of the Open Systems Interconnect (OSI) model. The physical layer is a serial, half-duplex RS-485 link on which reside a master (the host computer) and a number of slaves, each of which has its own unique address. The data link layer provides for packet transmission and reception and includes message verification using a checksum. The application layer comprises functions for data transfer between master and slave and certain system management functions. As implemented by Cimetrics, the application layer can be readily expanded to include custom functions specific to a particular system.

The communications software, e.g., that supplied by Cimetics Technology with the 9-Bit Solution, is based on the IEEE 1118 Microcontroller System Serial Control Bus standard and is an implementation of the NSP protocol. In that protocol, all communication is initiated by the master, and direct slave-to-slave communication is not permitted. Communication is done in packets of 9-bit characters, with the ninth bit being used to identify the first byte of a packet (ninth bit=1). In the case of messages from the master, the first byte contains the address of the intended recipient; in messages from a slave, the first byte is the slave's address. Generally a message from the master is addressed to just one slave, and that slave is obligated to respond to the message within a specified timeout interval. However, there is a reserved address for "broadcast" messages, which are intended for reception by all slaves and to which response is prohibited. There are also a number of other reserved addresses, so valid slave addresses range from 1 to 250.

In the instant embodiment, the software is adapted for a fluidics station having four identical hybridization modules, each having its own microcontroller and appearing to the master computer as an independent slave. A module in the fluidics station performs its functions, such as priming itself or hybridizing a chip, by executing a "hybridization script," which is a series of "hybridization commands" (described above) each terminated by an ASCII null character. Scripts are downloaded from the master using one of the GBS commands described below, and there are also commands for starting, stopping, and managing scripts. There can be just one script at a time in a module's internal script buffer.

Two of the GBS commands described below are involved in arranging for the execution of immediate mode commands. In the NSP protocol, each GBS command consists of a one-byte command code followed by zero or more bytes of parameters as required. Some of the commands may be of variable length: a byte elsewhere in the message containing the command tells the recipient how long the command is. Command codes in the range from 0x20 to 0x7F are reserved for custom commands, and so the codes for the commands described below are taken from that range.

For each GBS command in the NSP protocol, including custom commands, there must be a response that can be, and usually is, sent back to the master. Responses have the same format as commands: a one-byte response code followed by zero or more parameter bytes. Custom response codes are allowed, but in most cases the fluidics station uses response codes already defined by the protocol. Here the pre-defined codes are identified only by symbolic names. Custom codes are identified by symbolic names and numerical values.

The "Clear Script" (command code 0x20) command clears the buffer that holds the script and prepares it so that a new script can be downloaded into it. The command should be issued whenever a new script is to be downloaded. The "GBS"_PROTECTED" response is returned if a script is being executed at the time. It is not allowed to clear a script that is being executed. The "GBS_OK response is returned if the Clear Script command was successfully executed.

The "Download Script" (command code 0x24) command causes its parameter to be appended to the script buffer. The parameter for this command is a string of characters of any length up to the maximum that will fit into the communication buffer in the fluidics station. The string is appended unmodified to the script buffer.

Hybridization scripts will typically be much longer than the communication buffer in the fluidics station. Therefore, to download a script, the master will have to first issue a Clear Script command, then divide the script into short strings and download them one-at-a-time, in order, using Download Script commands. In dividing up the script, the master does not have to pay attention to the boundaries between hybridization commands within the script. It does, however, have to send the null characters that are used to terminate the hybridization commands. The "GBS_ PROTECTED" response is returned if there is a script in the script buffer that has been run at least once. Once a script has been executed, it is not allowed to download more commands to it. The "GBS_INSUFFICIENT_MEMORY" response is returned if there is not enough room in the script buffer for the additional bytes and the "GBS_OK" response is returned if the Download Script command was successfully executed.

The "Start Script" (command code 0x28) command starts execution of the script in the script buffer. The "GBS_ PROTECTED" response is returned if the script is already running. It is not allowed to start a script that is already being executed. The "GBS_OK" response is returned if the Start Script command was successfully executed.

The "Stop Script" (command code 0x2C) command stops execution of a script. The "GBS_OK" response is the only one returned to this command.

The "Report on Status" (command code 0x30) command causes the fluidics station to return information related to its status. The only response to this command is GBS_OK followed by a string of bytes giving information about the state of the given hybridization module and its associated script. The meanings of the bytes are as follows:

The "Script State" (byte 1) byte has the meanings shown in the table below:

TABLE I

Script State Byte Meaning S

| Value | Meaning |
| --- | --- |
| 0 | Script is idle. |
| 1 | Script is being executed. |
| 2 | Script stopped normally. |
| 3 | Script stopped because of an invalid command. |
| 4 | N/A |
| 5 | N/A |
| 6 | Script stopped because of a temperature timeout. |
| 7 | Script stopped because of a sensor timeout. |
| 8 | Script stopped because of a valve homing error. |
| 9 | Script stopped because of a valve motion error. |
| 10 | Script stopped because of a valve sensor error. |
| 11 | Script stopped because of a drain-and-fill error. |
| 12 | Script stopped because of a motor motion error. |

The "Command Offset" (bytes 2 and 3) is an integer, with its more significant byte in byte 2, that gives the offset with respect to the beginning of the script of the hybridization command most recently executed. If execution of a script stops abnormally, it can be used to locate the command where the abnormal condition occurred.

The "Script Stage" (byte 4) is the stage ID parameter of the most recently executed Enter Stage hybridization command. Its meaning is determined by agreement between the author of the hybridization script and the author of the software that runs on the master computer.

The "Enter Stage" hybridization command has the option of setting a timer to time the stage. Under those circumstances, the "Script Stage Flag" (byte 5) has the value 1 if the stage is still in progress and 2 if the timer has timed out. Otherwise, the flag has the value 0.

If the current hybridization stage is being timed, the "Script Stage Time Remaining" bytes (bytes 6–9) contain an unsigned long integer whose value gives the remaining time in tenths of a second. The bytes are in order from most significant to least.

The "Temperature" byte (bytes 10–11) is an integer, with the more significant byte first, giving the temperature at the cartridge holder in tenths of a degree C.

The "LCD Status" byte (byte 13) has the value '1' if there have been no timing errors in communication with the LCD in the fluidics station since a script was last started, and '0' otherwise.

The "Execute Immediate Command" (command code 0×34) command causes its parameter to be appended to the immediate command buffer and then causes the command in the buffer to be executed. The parameter for this command is a string of characters of any length up to the maximum that will fit into the communication buffer in the fluidics station. The string is appended unmodified to the immediate command buffer. Hybridization commands intended for immediate execution by the fluidics station may in principle be too long for the communication buffer. Thus, the Station provides a means for building such a command piece-by-piece and then executing it.

The "Accumulate Immediate Command" command described below can be used to insert all but the last piece of a command into the immediate command buffer, and then this command can be used to insert the last piece and cause the command to be executed. The "GBS_PROTECTED" response is returned if a script is being executed at the time. It is not allowed to execute an immediate command while a script is being executed. The "GBS_INSUFFICIENT_MEMORY" response is returned if there is not enough room in the immediate command buffer for the additional bytes. The "GBS_BAD_HYB_COMMAND"(code 0×20) response is returned if the fluidics station could not recognize or parse the contents of the immediate command buffer or if the command in the buffer was not one that can be executed in immediate mode. The "GBS_OK" response is returned if the hybridization command in the immediate command buffer was successfully executed.

The "Accumulate Immediate Command" (command code 0×38) command causes its parameter to be appended to the immediate command buffer. The parameter for this command is a string of characters of any length up to the maximum that will fit into the communication buffer in the fluidics station. The string is appended unmodified to the immediate command buffer. The "GBS_INSUFFICIENT_MEMORY" response is returned if there is not enough room in the immediate command buffer for the additional bytes. The "GBS_OK" response is returned if is the Accumulate Immediate Command command was successfully executed.

The "Read LCD Line" (command code 0×3C) command causes a string representing the contents of a particular line on the LCD to be returned in the response. The parameter for this command is a single digit specifying which line is to be read. An odd digit specifies line 1, an even digit, line 0 (the top line). The only possible response to this command is GBS_OK followed by an ASCII string representing the contents of the specified line on the LCD. The string is not null-terminated, so the message length should be used to determine how many characters are present.

The "Report Version" (command code 0×7F) command causes the fluidics station to report the version number of its firmware. The only possible response to this command is GBS_OK followed by an ASCII string giving the version number in the format major_version.minor_version, where both components of the number are decimal integers represented by one or more ASCII characters. The string is not null-terminated, so the message length should be used to determine how many characters are present.

After the fluidics station completes its power-on selftest and readies itself for communication with the master, it executes a short, internally generated script to home the distribution valve, synchronize the peristaltic pump with its driver, and perform other initialization functions. While that script is running, the response to a Report on Status command will show that the fluidics station is executing a script, and after the execution of the script is completed, the script buffer will have to be cleared before another script can be downloaded.

The above-described control software is merely provided as an example of a control system for operating the fluidics station of the invention. A variety of programs may be used to provide the same basic operations.

Figure 5:
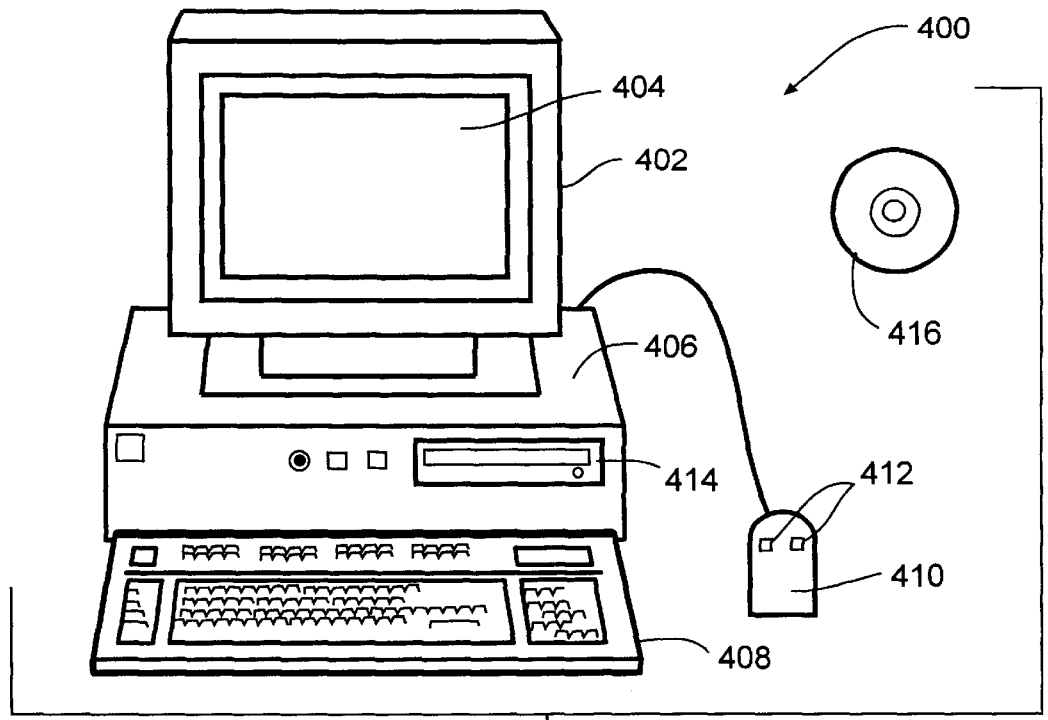
FIG. 5 is a schematic illustration of a computer system used to run software used for controlling the hybridization fluidics station of the invention.

In alternate aspects, overall control of the process may be provided by an external computer that is appropriately programmed to operate the above described systems according to an input set of process parameters. FIG. 5 shows a computer system 400 which includes a monitor 402, screen 404, cabinet 406, keyboard 408, and mouse 410. Mouse 410 may have one or more buttons such as mouse buttons 412. Cabinet 406 houses a CD-ROM drive 414 or a hard drive (not shown) which may be utilized to store and retrieve software including computer code programs incorporating the control system, digital images for use with the present invention, and the like. Although a CD-ROM 416 is shown as a computer readable medium for storing the computer programs including the present invention, other computer readable media including hard disks, floppy disks, DRAM, tape, and flash memory may be utilized. Cabinet 406 also houses familiar computer components (not shown) such as a processor, memory, and the like.

Figure 6:
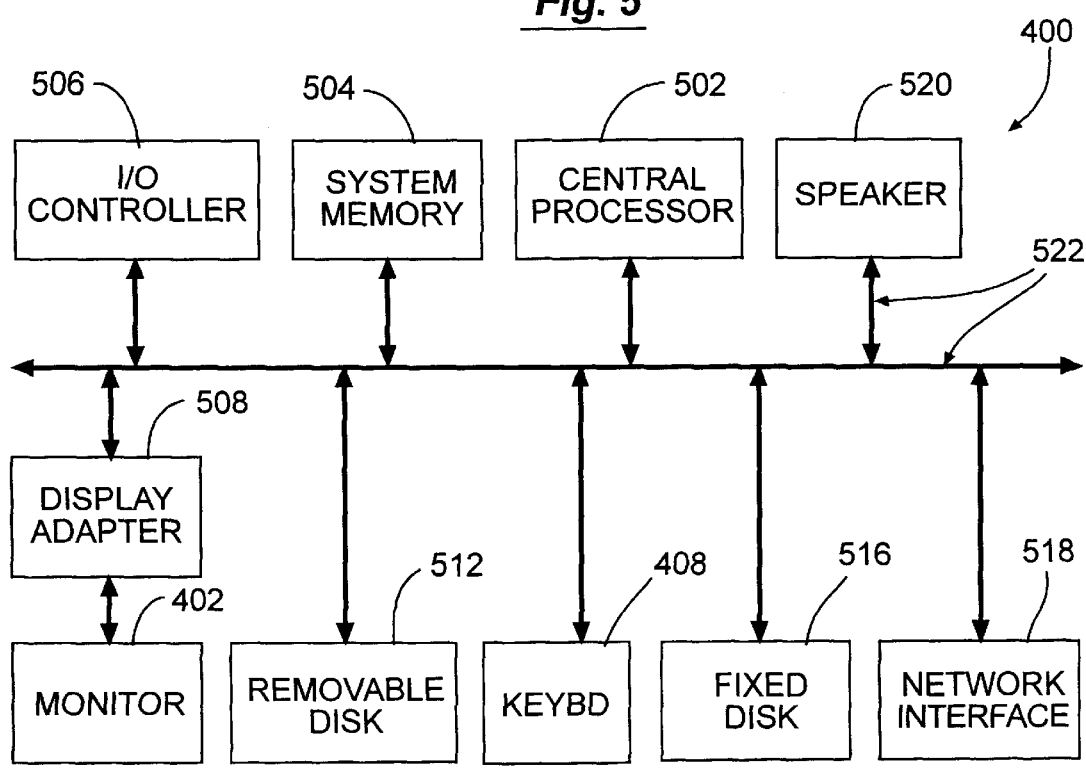
FIG. 6 shows a system block diagram of computer system shown in FIG. 5 used to execute the control software of the present invention.

FIG. 6 shows a system block diagram of computer system 400 used to execute the software of the present invention. As in FIG. 5 computer system 400 includes monitor 402 and keyboard 408. Computer system 400 further includes subsystems such as a central processor 502, system memory 504, I/O controller 506, display adapter 508, removable disk 512, fixed disk 516, network interface 518, and speaker 520. Other computer systems suitable for use with the present invention may include additional or fewer subsystems. For example, another computer system could include more than one processor 502 (i.e., a multi-processor system) or a cache memory.

Arrows such as 522 represent the system bus architecture of computer system 400. However, these arrows are illustrative of any interconnection scheme serving to link the subsystems. For example, a local bus could be utilized to connect the central processor to the system memory and display adapter. Computer system 400 shown in FIGS. 4 and 5 is but an example of a computer system suitable for use with the present invention. Other configurations of subsystems suitable for use with the present invention will be readily apparent to one of ordinary skill in the art.

III. Fluidics Station Operation

The fluidics station is operated to deliver reagents, samples (e.g., analytes), buffer and wash solutions to the hybridization chamber, and to maintain optimal reaction conditions, e.g., temperature and mixing, within the hybridization chamber for a preselected time (FIG. 4) or number of cycles. Operation of the hybridization chamber begins with the insertion of an array cartridge 100 into one of the modules 300 of the station 400 (see FIG. 3A). The array cartridge, as previously described, is inserted into the open mounting frame 302 of the device. As described previously, insertion of the cartridge into the mounting frame will automatically align the cartridge for subsequent operations by virtue of the inclusion of alignment structures on the frame as well as the cartridge. Once the cartridge is inserted, the mounting frame, which is generally a hinged door, is closed and secured against the mounting plate 350 which may also include alignment structures for proper alignment of the cartridge. The mounting frame also typically includes the temperature controller element 356.

While the array cartridge is secured in the mounting system, the injection needles 358, 360 may be inserted through the inlet 130 and outlet 134 of the cartridge 100. As previously described, these injection needles may be retractable or may be disposed in the fluidics station whereby they are automatically inserted into the inlet and outlet of the array cartridge by virtue of the operation of securing of the array cartridge within the mounting system. Optionally, one or more sensors, such as optical sensors, may be provided to determine when the frame is closed and when the injection needles are inserted into the cartridge.

Once the array cartridge is secured within the fluidics station, the pump 206 delivers an initial solution to the hybridization chamber. This first solution is may be a buffer solution or a sample-containing solution, e.g., containing a target nucleic acid. The chamber is filled for a set time period, or, in the case of buffers having detectable conductivity, until the sensor on the outlet side of the hybridization chamber indicates that the chamber is filled. The chamber may then be brought to an appropriate temperature by the temperature controller element.

Typically, samples include a target nucleic acid that incorporates a fluorescent or gold label for subsequent detection. The chamber is maintained at an appropriate temperature for the particular hybridization reaction. Appropriate temperatures are generally in the range of acceptable biological temperatures, e.g., from about 30° C. to about 40° C., but will often vary from this range, depending upon the reaction being performed, or the nature of the species involved in the hybridization. For example, for hybridization of nucleic acids that are richer in A and T bases, hybridization may be carried out at lower temperatures, whereas GC rich nucleic acids may generally be hybridized at higher temperatures.

Although static hybridization reactions may be performed in the chamber, it is generally preferred to provide mixing, agitation or convection within the hybridization chamber to ensure maximal presentation of the sample to the array. Accordingly, the fluidics station of the present invention typically includes a mixing system. While a variety of mixing systems have been described, a preferred mixing system utilizes the pump for the fluidics station and performs what is termed a "drain and fill" operation. As the name indicates, this involves repeated draining and filling of the hybridization chamber with the sample. In operation, once the chamber is initially filled, the drain and fill operation involves the reversal of the pump which draws the sample out of the hybridization chamber. When the sensor at the inlet of the hybridization chamber indicates the presence of air, i.e. a large drop in conductivity, the pump is reversed to refill the hybridization chamber. During this operation, the sample is either being returned to its vial or is retained in the void volume of the tubing of the device. Thus, little or no sample volume is lost during this operation. Mixing is generally carried out according to an optimized profile that may be easily developed depending upon the nature of the reaction being performed.

Following hybridization for a preselected time period, the fluidics station will typically deliver a wash solution, and/or buffer to the hybridization chamber, to rinse substantially all of the sample containing solution from the chamber. This avoids any difficulty associated with sample remaining in the background, e.g., background fluorescence, that can impede clear and accurate determinations of hybridization. Wash steps will typically be repeated as desired, to sufficiently reduce or eliminate any remaining, unhybridized target. Typically, the wash steps will be repeated from two to ten times.

Following washing, the hybridization chamber may be filled with an appropriate solution for scanning the array. Such solutions generally include buffers, water or the like. Typically, the wash solution is the same as the buffer solution. Once completed, the array cartridge is transferred to a reader/scanner device to identify the locations on the array to which the target hybridized. Such scanner devices have been described in, e.g., U.S. Pat. No. 5,143,854, Published PCT Application Nos. WO 90/15070 and 92/10092, previously incorporated herein by reference, as well as U.S. patent application Ser. Nos. 08/195,889, filed Feb. 10, 1994, and 08/301,051, filed Sep. 2, 1994, each of which is hereby incorporated herein by reference in its entirety for all purposes.

IV. Additional Elements

In addition to the above described elements, the fluidics stations of the present invention may incorporate a wide variety of modifications to enhance their usefulness and ease of operation in performing hybridization reactions. For example, the fluidics stations of the present invention will typically include multiple modules, e.g., single fluidics units, each module being capable of performing hybridization reactions on a separate array cartridge. These multiple modules may perform parallel reactions, i.e., the same reaction on multiple array cartridges, or may perform a number of different hybridizations on separate array cartridges.

An example of the modular design of the fluidics station is shown in FIG. 2, wherein additional fluidics modules 240, 250 and 260 are illustrated as fluidly connected to the fluid delivery system. Typically, each of these modules may be isolated from the others with respect to the fluid delivery, temperature control and process control systems such that multiple independent operations may be carried out at each module. The modular design also allows removal of a particular module for repair or replacement without affecting the remaining modules.

Each fluidics module may also be provided with an appropriate display, e.g., an LCD readout as described above in the description of the control system and as shown in FIGS. 3A and 4, which displays the status of the particular fluidics module, e.g., time of operation, temperature of hybridization reaction, description of operation being performed, etc.

Figure 8A:
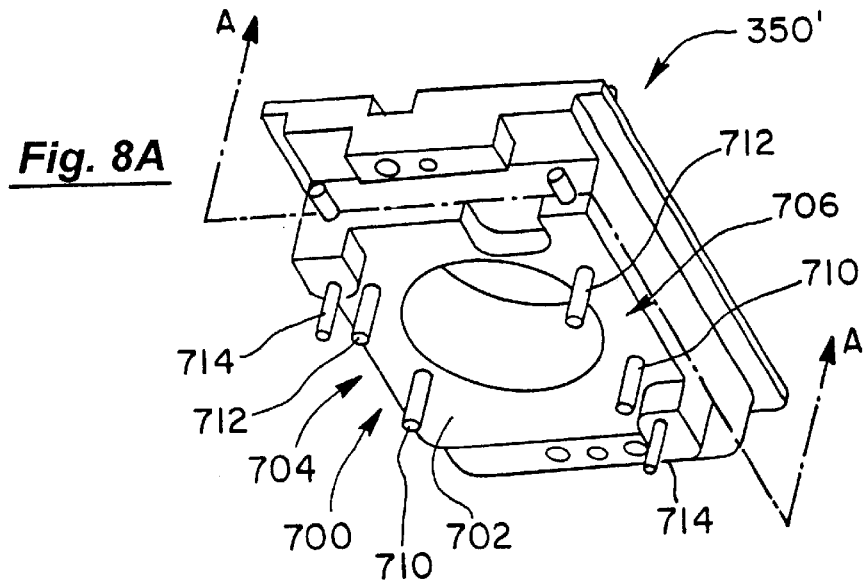
FIG. 8A is a perspective view of an exemplary sensing system for sensing the presence of fluids according to the invention.
Figure 8B:
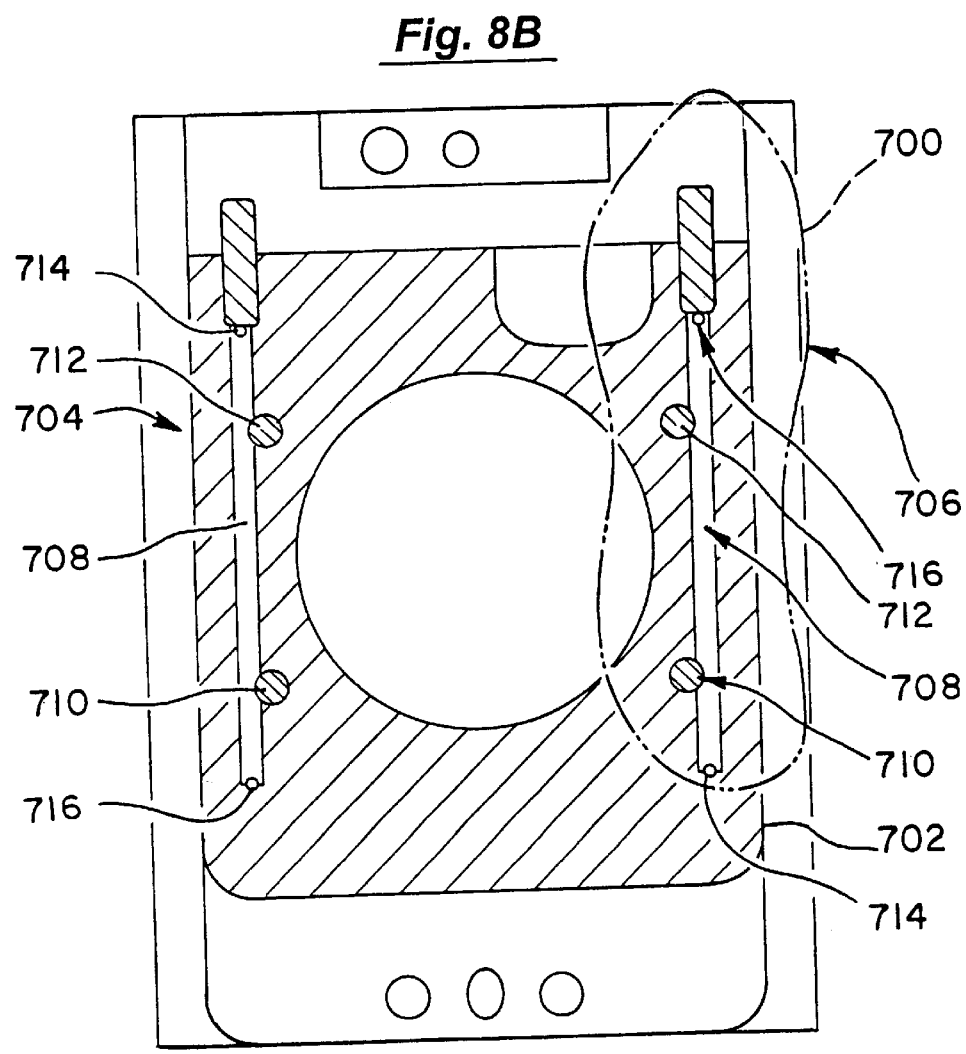
FIG. 8B is a cross sectional view of the sensing system of FIG. 8A taken along lines A—A.

As illustrated in FIGS. 8A and 8B, a mounting plate 350' may include a sensing system 700 to sense the presence or absence of fluid near the fluid inlet and outlet of cartridge 100. Such information is then used to drain, stop draining, fill or stop filling cartridge 100. The sensing system of FIG. 8 is included in a single machined block which tightly controls the physical geometry of the sensor, lessening unit to unit variability, while also simplifying assembly and service to the system.

System 700 comprises a sensor block 702 having two parallel sensors 704 and 706. Sensor 704 monitors the input to cartridge 100 while sensor 706 monitors the output of cartridge 100. As also shown in FIG. 8B sensors 704 and 706 each comprise a channel 708 intersected by two conductive pins 710, 712 which are generally perpendicular to channel 708. Pins 710, 712 are positioned such that they only slightly impede the fluid path. At the ends of each channel 708 are holes into which needles 714 and 716 are pressed. Needles 716 include a ball end and a sideport to interface with cartridge 100. The blunt end of needles 716 prevents the septa in cartridge 100 from being damaged, thereby promoting sealing. Needles 714 are provided to interface with the fluidics station.

Channels 708 are preferably oriented vertically to promote maximum drainage and to accommodate physical packaging requirements. Needles 716 are parallel to each other and exit the front of block 702 to interface with cartridge 100. Pins 710, 712 protrude from block 702 on a back side and are electrically connected to the fluidics station using push on, spring loaded connectors that are mounted to a single board. Preferably, pins 710, 712 are constructed of 316 Stainless Steel to prevent corrosion. Block 702 is preferably constructed of Delrin, an acetyl plastic, to provide sealing. Preferably, three wires are electrically connected to pins 710, 712, with the pins nearer the package interface being joined together and held at ground potential. The presence or absence of a liquid within channels 708 may then be determined by evaluating the potential difference between pins 710 and 712.

Figure 9:
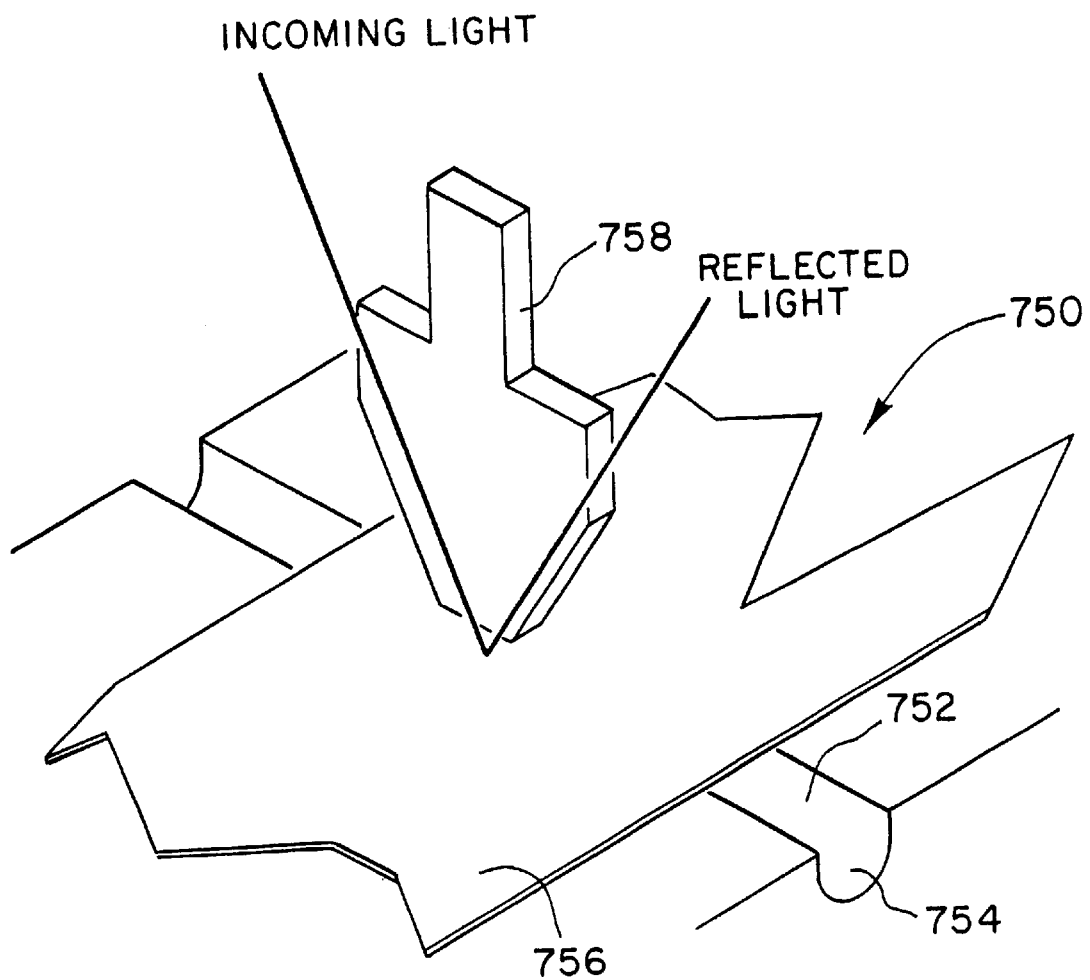
FIG. 9 is a schematic view of an alternative sensing system according to the invention.

An alternative fluid sensing system 750 is illustrated in FIG. 9 and is particularly useful in detecting the presence or absence of a fluid in a disposable, closed system, such as may be employed in the fluidics stations described herein. System 750 comprises a sensing cavity 752 which is constructed by forming a slot 754 in a block of material. A transparent material 756 is then placed over slot 754 to create a channel which is open at two ends. The presence or absence of a liquid in channel 754 is determined with a photodetector 758 which has a light source to project light through material 756. The internal surface of material 756 is used as the only active wall of the sensing cavity 752. Depending on the nature of the reflected light as measured by photodector 758, the pressure or absence of a liquid may be determined. Optionally, an aperture plate may be installed to increase the signal to noise ratio by blocking some, or all, of the light reflected of the front surface of material 756. Additionally, the light may be focused to spatially filter the signal. Some masking may also be used to improve discrimination. Once the presence or absence of a liquid has been detected, a signal may be sent from photodetector 758 to an electronic controller which controls the liquid flowing in the fluidics station.

While the foregoing invention has been described in some detail for purposes of clarity and understanding, it will be clear to one skilled in the art from a reading of this disclosure that various changesin form and detail can be made without departing from the true scope of the invention. All publications and patent documents cited in this application are incorporated by reference in their entirety for all purposes to the same extent as if each individual publication or patent document were so individually denoted.

What is claimed is:

1. A fluidics station comprising:
   a base that is adapted to provide framework for the fluidics station;
   a mounting system coupled to the base, the mounting system comprising a mounting member adapted to receive a cartridge, and wherein the mounting system is movable between a loading position and a closed position;
   at least two needles coupled to the base frame, wherein the needles each include a distal end and side ports above the distal ends; and
   at least one fluid source in communication with at least one of the needles;
   wherein the cartridge is insertable into the mounting system when in the loading position, and wherein the needles are adapted to be inserted into the cartridge when in the closed position.

2. A station as in claim 1, wherein the mounting member comprises a mounting frame having a slot adapted to receive the cartridge, and wherein the mounting frame is coupled to the base frame by a hinge.

3. A station as in claim 1, wherein the slot is keyed such that the cartridge is insertable into the mounting frame in only one orientation.

4. A station as in claim 1, wherein the mounting system includes a shunt element which in the absence of a cartridge receives the needles when in the closed position to allow fluids to flow between the two needles.

5. A station as in claim 1, further comprising a temperature controlling element coupled to the base, the temperature controlling element being adapted to contact the cartridge when the mounting system is in the closed position.

6. A station as in claim 5, further comprising a tube coupling the fluid source to one of the needles, and wherein at least a portion of the tube is disposed near the temperature controlling element.

7. An apparatus for processing a fluid sample, comprising:
   a cartridge having a chamber, the chamber having disposed therein an array of probes, the array of probes including a plurality of different nucleic acid sequences coupled to a solid support in different known locations;
   a fluid delivery system for delivering a sample to the chamber, the fluid delivery system including an input needle and an output needle, wherein the needles include blunt distal ends and side ports through which fluids may pass; and
   a cartridge mounting system that is adapted to be moved between an loading position and a closed position, wherein the needles are adapted to be coupled to the chamber when the cartridge mounting system in the closed position.

8. The apparatus of claim 7, wherein the fluid delivery system comprises:
   a pump in fluid communication with the chamber when the fluid delivery system is coupled to the chamber;
   a sample vessel;
   a plurality of individual reagent vessels; and
   a valve structure in communication with the pump, the valve structure being disposed between the chamber and the sample vessel and reagent vessels to individually connect each of the reagent vessels and the sample vessel to the pump such that operation of the valve structure places the sample vessel or one of the reagent vessels in fluid communication with the pump to allow the pump to deliver a fluid from the sample vessel or the reagent vessel to the chamber; and a first length of tubing connecting the sample vessel to the pump and a second length of tubing connecting the pump to the chamber.

9. The apparatus of claim 8, wherein the pump is a peristaltic pump.

10. The apparatus of claim 8, wherein the pump is a syringe pump.

11. The apparatus of claim 7, further comprising a mixing system positioned to mix the sample in the chamber, wherein the mixing system comprises a piezoelectric element disposed adjacent the chamber, whereby operation of the piezoelectric element produces a convective effect in the chamber.

12. The apparatus of claim 7, further comprising a mixing system positioned to mix the sample in the chamber, wherein the mixing system comprises a reversible pump for removing and redelivering the sample fluid out of and into the chamber.

13. An apparatus for processing fluids, comprising:
a fluid delivery system adapted to deliver fluids into an array cartridge, the array cartridge including a chamber having a probe array incorporated therein;
a mounting system which is adapted to removably hold the chamber within the array cartridge in fluid communication with the fluid delivery system, the mounting system having an loading position for receiving the cartridge and a closed position wherein the cartridge is positioned to be coupled with the fluid delivery system;
a temperature control system for monitoring and controlling a temperature of the fluids within the chamber;
an injection system to couple the fluid delivery system to the array cartridge when the mounting system is moved to the closed position, wherein the injection system comprises an inlet needle and an outlet needle, wherein each of the needles includes a blunt end and side ports for passing fluids; and
a process control system for monitoring and controlling the fluid delivery system and the temperature control system.

14. An apparatus as in claim 13, wherein the temperature control system comprises a temperature controlled block which is placed adjacent an external surface of the array cartridge when the cartridge is in the mounting system and the mounting system moved to the closed position.

15. The apparatus of claim 13, wherein the fluid delivery system includes one or more sensors for determining when the chamber is filled or drained.

16. The apparatus of claim 15, wherein the one or more sensors are selected from the group consisting of conductivity sensors and optical sensors.

17. The apparatus of claims 14, wherein the temperature controlled block comprises a thermoelectric temperature controlled element.

18. The apparatus of claim 13, wherein the mounting system comprises a mounting frame and a mounting plate, the mounting plate being adapted to receive the array cartridge, and the mounting frame being operably connected to the mounting plate to hold the mounting plate, the mounting frame and mounting plate being adapted to hold the array cartridge in fluid communication with the fluid delivery system.

19. The apparatus of claim 13, wherein the mounting system comprises alignment structures for aligning the array cartridge on the mounting system.

20. A method for introducing a fluid into a cartridge, the method comprising:
providing a frame, at least two needles coupled to the frame, wherein needles includes a distal end and a side port, and a mounting system that is coupled to the frame, wherein mounting system is movable between a loading position and a closed position;
placing at least one fluid source in communication with at least one of the needles;
inserting a cartridge into the mounting system while in the loading position;
moving the mounting system to the closed position to insert the distal end of the needles into the cartridge; and
transferring fluid from the source into the cartridge through the side port of one of the needles.

21. A method as in claim 20, further comprising inserting the distal ends through a septa in the cartridge.

22. A method as in claim 20, further comprising removing the fluid from the cartridge through the side port of the other needle.

23. A method as in claim 22, further comprising discarding the removed fluid.

24. A method as in claim 22, further comprising recirculating the removed fluid through the cartridge.

25. A method as in claim 20, wherein the mounting system further includes a shunt and further comprising removing the cartridge, placing the mounting system in the closed position to insert the needles into the shunt of the mounting system, and circulating a washing solution through the shunt.

26. A method as in claim 25, further comprising removing and discarding the shunt.

27. A method as in claim 20, wherein a temperature controlling elements is coupled to the frame, and further comprising contacting the temperature controlling element with the cartridge when the mounting system is placed in the closed position.

28. A method as in claim 27, further comprising altering the temperature of the transferred fluid with the temperature controlling element as the fluid is transferred to the cartridge and while the fluid is within the cartridge.

29. A method for staining a hybridization array, comprising:
providing a station having a fluid delivery system to deliver at least one fluid from at least one vessel into an array cartridge, the array cartridge including a chamber having a hybridization array, and a mounting system for removably holding the chamber within the array cartridge in fluid communication with the fluid delivery system, the mounting system having an loading position for receiving the cartridge and a closed position wherein the cartridge is positioned to be coupled with the fluid delivery system;
inserting the cartridge into the mounting system in the loading position and moving the mounting the system to the closed position where the fluid delivery system is coupled to the cartridge; and
delivering a stain from the vessel into the chamber of the cartridge with the fluid delivery system to stain the array.

30. A method as in claim 29, further comprising removing the stain from the chamber with the fluid delivery system.

31. A method as in claim 30, further comprising recovering the removed stain.

32. A method as in claim 29, further comprising washing the stained array.

33. A method for washing a hybridization array, comprising:

provinding a station having a fluid delivery system to deliver at least one fluid from at least one vessel into an array cartridge, the array cartridge including a chamber having a hybridization array, and a mounting system for removably holding the chamber within the array cartridge in fluid communication with the fluid delivery system, the mounting system having an loading position for receiving the cartridge and a closed position wherein the cartridge is positioned to be coupled with the fluid delivery system;

inserting the cartridge into the mounting system and moving the mounting system to the closed position where the fluid delivery system is coupled to the cartridge;

delivering a washing fluid from the vessel into the chamber of the cartridge with the fluid delivery system to wash the array.

34. A method as in claim 33, further comprising introducing a sample from at least one vessel and into the chamber using the fluid delivery system, and removing and recovering the sample from the chamber with the fluid delivery system.

* * * * *

UNITED STATES PATENT AND TRADEMARK OFFICE
CERTIFICATE OF CORRECTION

PATENT NO.    : 6,391,623 B1
DATED         : May 21, 2002
INVENTOR(S)   : Donald Besemer et al.

It is certified that error appears in the above-identified patent and that said Letters Patent is hereby corrected as shown below:

Title page,
Item [54], the title should be -- FLUIDICS STATION INJECTION NEEDLES WITH BLUNT DISTAL END AND SIDE PORTS AND METHOD OF USING. --

Column 24,
Table I, delete "Meaning S" form the title of Table I and insert therefor -- Meanings --.

Column 30,
Line 7, insert -- a -- after "provide".
Line 54, replace "an" with -- a --.
Line 56, insert -- is -- after "system."

Column 31,
Line 32, replace "an" with -- a --.
Line 57, delete "claims" and replace with -- claim --.

Column 32,
Line 7, after "wherein", insert -- each --.
Line 7, delete "needles" and replace with -- needle --.
Line 37, delete "elements" and replace with -- element --.
Line 53, replace "an" with -- a --.

Column 33,
Line 11, replace "an" with -- a --.

Signed and Sealed this

Seventh Day of January, 2003

JAMES E. ROGAN
*Director of the United States Patent and Trademark Office*